US011593348B2

(12) United States Patent
Muse et al.

(10) Patent No.: US 11,593,348 B2
(45) Date of Patent: Feb. 28, 2023

(54) PROGRAMMATICALLY MANAGING PARTIAL DATA OWNERSHIP AND ACCESS TO RECORD DATA OBJECTS STORED IN NETWORK ACCESSIBLE DATABASES

(71) Applicant: Optum, Inc., Minnetonka, MN (US)

(72) Inventors: Jon Kevin Muse, Thompson Station, TN (US); Gregory J. Boss, Saginaw, MI (US); Rick A. Hamilton, Charlottesville, VA (US); Charles P. Schaller, Minnetonka, MN (US)

(73) Assignee: Optum, Inc., Minnetonka, MN (US)

( * ) Notice: Subject to any disclaimer, the term of this patent is extended or adjusted under 35 U.S.C. 154(b) by 189 days.

(21) Appl. No.: 16/803,776

(22) Filed: Feb. 27, 2020

(65) Prior Publication Data

US 2021/0271662 A1 Sep. 2, 2021

(51) Int. Cl.
*G06F 16/23* (2019.01)
*G06F 21/62* (2013.01)
(Continued)

(52) U.S. Cl.
CPC .......... *G06F 16/2365* (2019.01); *H04L 63/08* (2013.01); *G06F 2221/2141* (2013.01)

(58) Field of Classification Search
CPC ............. G06F 16/2365; G06F 21/6245; G06F 2221/2141; H04L 63/08; G16H 50/70; G16H 10/60
See application file for complete search history.

(56) References Cited

U.S. PATENT DOCUMENTS 7,558,793 B1 * 7/2009 Topolovac ......... G06Q 10/0875
707/999.009
9,646,169 B2 * 5/2017 Wong ..................... H04L 63/10
(Continued)

FOREIGN PATENT DOCUMENTS

WO WO-2008155704 A2 * 12/2008 ............. G16H 10/65
WO 2015/183828 A1 12/2015

OTHER PUBLICATIONS

M. F. F. Khan and K. Sakamura, "Fine-grained access control to medical records in digital healthcare enterprises," 2015 International Symposium on Networks, Computers and Communications (ISNCC), 2015, pp. 1-6, doi: 10.1109/ISNCC.2015.7238590. (Year: 2015).*

(Continued)

*Primary Examiner* — Dennis Truong
(74) *Attorney, Agent, or Firm* — Alston & Bird LLP

(57) ABSTRACT

Data ownership of a single record data object comprising a plurality of individual data elements may be distributed across a plurality of users, such that each individual user is capable of separately controlling access to those data elements for which the data owner has ownership privileges. These data ownership privileges, and corresponding access rights which may be individually provided by distinct data owners, is managed by a data management computing entity such that a single composite user interface may be generated for a user viewing a particular record data object such that the viewer is provided with viewing access to only those data elements for which the viewer has access. Thus, separate user interfaces may be generated and provided for different viewers accessing the same record data object.

20 Claims, 13 Drawing Sheets

(51) Int. Cl.
   *H04L 9/40*        (2022.01)
   *G16H 50/70*       (2018.01)
   *G16H 10/60*       (2018.01)

(56) References Cited

U.S. PATENT DOCUMENTS

| | | | |
|---|---|---|---|
| 10,185,809 B1 | 1/2019 | Zhou et al. | |
| 2002/0010679 A1* | 1/2002 | Felsher | G06Q 20/3674 |
| | | | 705/51 |
| 2004/0199765 A1* | 10/2004 | Kohane | H04L 63/10 |
| | | | 713/165 |
| 2006/0229918 A1* | 10/2006 | Fotsch | G16H 10/60 |
| | | | 705/3 |
| 2007/0192137 A1* | 8/2007 | Ombrellaro | G06Q 10/10 |
| | | | 705/2 |
| 2009/0076994 A1* | 3/2009 | Ghosh | G06N 5/00 |
| | | | 706/46 |
| 2009/0326981 A1 | 12/2009 | Karkanias et al. | |
| 2010/0241595 A1* | 9/2010 | Felsher | G06Q 10/10 |
| | | | 705/400 |
| 2010/0262837 A1 | 10/2010 | Kulin | |
| 2012/0110642 A1* | 5/2012 | Grassel | G06Q 10/101 |
| | | | 726/4 |
| 2012/0143013 A1 | 6/2012 | Davis, III et al. | |
| 2012/0197873 A1* | 8/2012 | Uramoto | G07B 15/06 |
| | | | 707/E17.014 |
| 2012/0232929 A1* | 9/2012 | Experton | G16H 10/65 |
| | | | 705/3 |
| 2014/0257047 A1* | 9/2014 | Sillay | A61B 5/4082 |
| | | | 600/301 |
| 2014/0372250 A1* | 12/2014 | Dugan | G06Q 30/0631 |
| | | | 705/26.7 |
| 2015/0101065 A1* | 4/2015 | Sullivan | H04L 63/101 |
| | | | 726/28 |
| 2016/0063273 A1* | 3/2016 | Wong | G06F 16/951 |
| | | | 707/785 |
| 2018/0053012 A1 | 2/2018 | Myers et al. | |
| 2018/0091413 A1 | 3/2018 | Richards et al. | |
| 2018/0330113 A1* | 11/2018 | McGrath | G06F 16/2282 |
| 2018/0358117 A1* | 12/2018 | Neagle | A61B 5/332 |
| 2019/0074072 A1 | 3/2019 | Aldridge et al. | |
| 2019/0243911 A1 | 8/2019 | Kobozev et al. | |
| 2019/0245871 A1* | 8/2019 | Ward | H04L 63/1416 |

OTHER PUBLICATIONS

W.-T. Tsai and Q. Shao, "Role-Based Access-Control Using Reference Ontology in Clouds," 2011 Tenth International Symposium on Autonomous Decentralized Systems, 2011, pp. 121-128, doi: 10.1109/ISADS.2011.21. (Year: 2011).*

K. Czajkowski, C. Kesselman and R. Schuler, "ERMRest: A Collaborative Data Catalog with Fine Grain Access Control," 2017 IEEE 13th International Conference on e-Science (e-Science), 2017, pp. 510-517, doi: 10.1109/eScience.2017.83. (Year: 2017).*

"Enhanced Patient Matching Is Critical To Achieving Full Promise Of Digital Health Records," A Report From The Pew Charitable Trusts, Oct. 2018, (50 pages). [Retrieved from the Internet Mar. 2, 2020] <https://www.pewtrusts.org/en/research-and-analysis/reports/2018/10/02/enhanced-patient-matching-critical-to-achieving-full-promise-of-digital-health-records>.

Abouelmehdi, Karim. "Big Healthcare Data: Preserving Security and Privacy," Journal of Big Data, Dec. 2018, vol. 5, No. 1, pp. 1-18. DOI: 10.1186/s40537-017-0110-7.

* cited by examiner

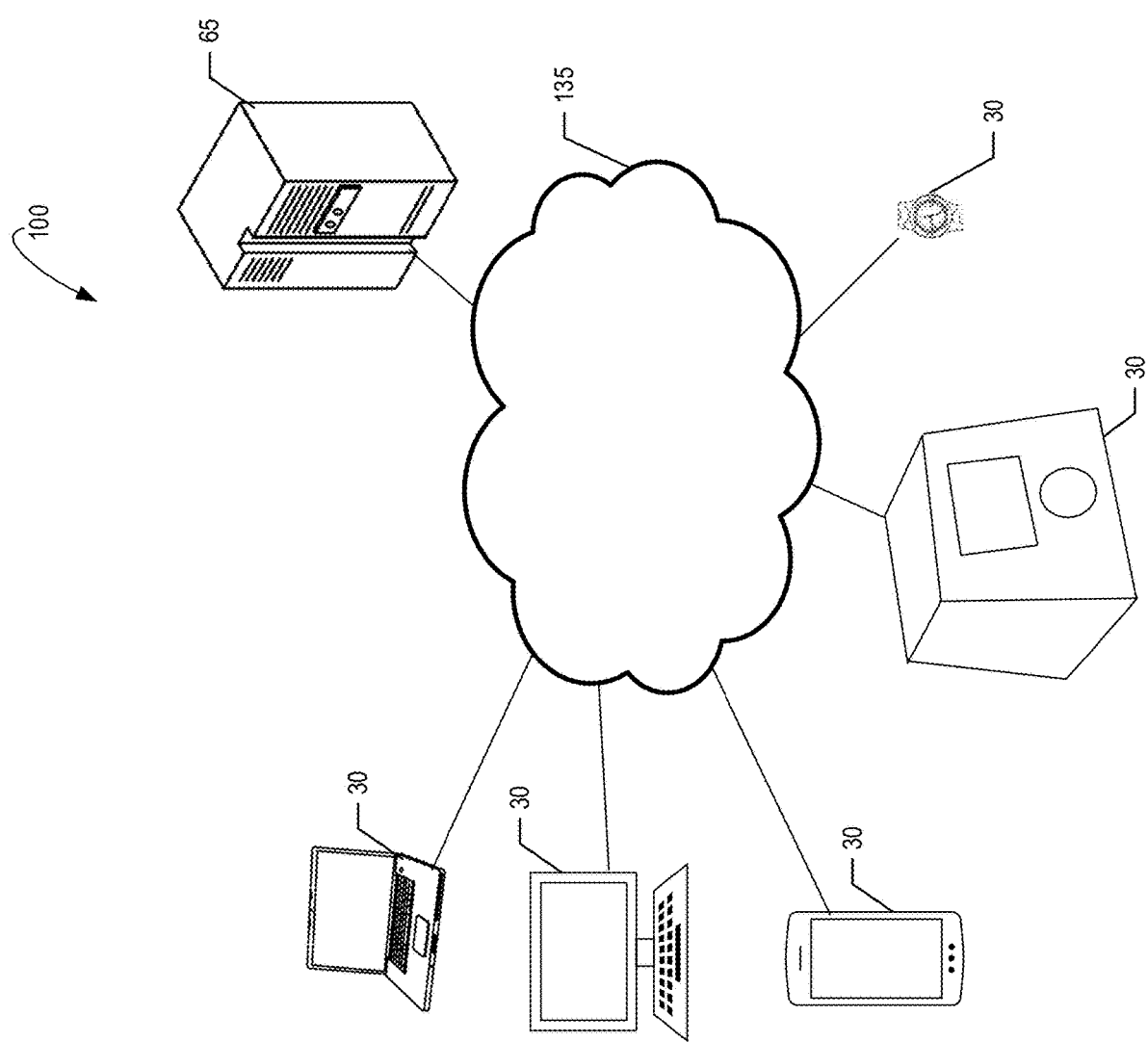

PROGRAMMATICALLY MANAGING PARTIAL DATA OWNERSHIP AND ACCESS TO RECORD DATA OBJECTS STORED IN NETWORK ACCESSIBLE DATABASES

BACKGROUND

With the increasing prevalence of wearable sensors/devices and home-based Internet of Things sensors/devices, as well as the ever-increasing number of data generating systems and devices, management of this growing quantity of data is becoming increasingly important. For example, within the medical industry, data that may be correlated with a patient/user's healthcare is constantly being generated by wearable devices (e.g., blood pressure sensors, body temperature sensors, blood-oxygen sensors, glucose sensors, and/or the like), as well as via newly developed testing devices that may be utilized at home or within a hospital or other medical location. This newly developed data, as well as existing patient-related healthcare data (e.g., Electronic Medical Records—referred to as EMR data; Electronic Health Records (EHR) data; Individual Health Records (IHR) data; and/or the like) may provide insights into a patient's health. However, at present, these various data types are generally not correlated due to various technical and privacy-related challenges.

Through applied effort and ingenuity, various limitations existing within the art have been addressed by certain embodiments as discussed herein.

BRIEF SUMMARY

Various embodiments are directed to data management systems that may be implemented to manage data stored within centralized data storage repositories and/or within distributed data storage repositories. To maintain appropriate levels of privacy over the data, the data management systems attribute ownership data to individual pieces of data stored within the data storage repositories, such that appropriate data owners may have management access to the data. Thus, even within a record of related data (e.g., within a patient's medical record), individual pieces of data may have different ownership attributions, thereby preventing unauthorized access to specific aspects of data stored therein, while enabling appropriate levels of access to other pieces of data. Such data management systems additionally facilitate transfers of data ownership and/or assignments of various data access rights to other users, for example, by providing data transfer authorization requests that may be provided to data owners via any of a variety of communication channels. Finally, various embodiments are configured for generating consolidated composite user interfaces for record data objects, such that a single user interface for a record data object comprises data having differing ownership attributions, and for ensuring that data that is not authorized for viewing by a requesting user is hidden and/or otherwise inaccessible to the viewer.

Various embodiments are directed to an electronic record data object storage system configured for maintaining a plurality of record data objects each comprising a plurality of data elements, the system comprising: one or more memory storage repositories storing one or more record data objects each comprising a plurality of data elements, wherein each of the one or more record data objects comprises access data for each data element stored therein, and wherein the access data for each data element has associated ownership data identifying access credentials of the data element and wherein the record data object comprises a first data element identifying first access credentials associated with a first user identifier and a second data element identifying second access credentials associated with a second user identifier; one or more processors collectively configured to: receive a record data object access request for a particular record data object, wherein the record data object access request is associated with a requesting user identifier; retrieve access data associated with the particular record data object; and generate a user interface for the record data object by: identifying one or more authorized data elements from the one or more data elements stored within the particular record data object, wherein the one or more authorized data elements have associated ownership data identifying the requesting user identifier; and populating one or more user interface data elements of the user interface with the one or more authorized data elements.

In various embodiments, the record data object access request identifies a requested data element of the particular record data object, and wherein the one or more processors are collectively further configured to: determine whether the requesting user identifier is identified within the ownership data associated with the requested data element; upon determining that the requesting user identifier is identified within the ownership data associated with the requested data element, populate one or more user interface data elements of the user interface with the requested data element; upon determining that the requesting user identifier is not identified within the ownership data associated with the requested data element, transmit an access request notification to a user computing entity associated with a user identifier included within the ownership data of the requested data element; and upon receipt of an approval response from the user computing entity associated with the user identifier included within the ownership data of the requested data element, populate one or more user interface data elements of the user interface with the requested data element.

In certain embodiments, the one or more memory storage repositories store the one or more record data objects in one or more relational database tables, wherein each of the one or more data elements are reflected within corresponding entries of the database tables, and wherein the ownership data is reflected within entries associated with the one or more data elements. In various embodiments, the one or more memory storage repositories are embodied as distributed memory storage areas, and wherein the one or more processors are associated with a central data management computing entity. In certain embodiments, the central data management computing entity additionally comprises data management storage areas storing ownership data corresponding to data elements stored within a plurality of distributed memory storage areas. In various embodiments, the one or more processors are further configured to: receive an ownership transfer request from a user computing entity for a specific data element of a record data object; determine a current owner of the specific data element; transmit an ownership transfer request notification to a user computing entity associated with the current owner of the specific data element; and upon receipt of a transfer approval from the user computing entity associated with the current owner of the specific data element, update ownership data associated with the specific data element.

In certain embodiments, the one or more processors are further configured to, upon receipt of the ownership transfer request for the specific data element of the record data object: determine a current owner of the record data object; transmit an ownership transfer request notification to a user computing entity associated with the current owner of the record data object associated with the specific data element; and upon receipt of the transfer approval from the user computing entity associated with the current owner of the specific data element and a second transfer approval from the user computing entity associated with the current owner of the record data object, update ownership data associated with the specific data element. In various embodiments, the one or more processors are further configured to: receive a new data element from a user computing entity, wherein the new data element has corresponding metadata identifying the user computing entity; based at least in part on the metadata, identify a record data object corresponding to the data element; and based at least in part on the identified record data object corresponding to the data element and the metadata, identify ownership data corresponding with the new data element.

Certain embodiments are directed to a computer-implemented method for maintaining a plurality of record data objects each comprising a plurality of data elements, the method comprising: storing, within one or more memory storage repositories, one or more record data objects each comprising a plurality of data elements, wherein each of the one or more record data objects comprises access data for each data element stored therein, and wherein the access data for each data element has associated ownership data identifying access credentials of the data element and wherein the record data object comprises a first data element identifying first access credentials associated with a first user identifier and a second data element identifying second access credentials associated with a second user identifier; receiving, via one or more processors, a record data object access request for a particular record data object, wherein the record data object access request is associated with a requesting user identifier; retrieving, via the one or more processors, access data associated with the particular record data object; generating a user interface for the record data object, via the one or more processors, by: identifying one or more authorized data elements from the one or more data elements stored within the particular record data object, wherein the one or more authorized data elements have associated ownership data identifying the requesting user identifier; and populating one or more user interface data elements of the user interface with the one or more authorized data elements.

In certain embodiments, the record data object access request identifies a requested data element of the particular record data object, and wherein the method further comprises: determining whether the requesting user identifier is identified within the ownership data associated with the requested data element; upon determining that the requesting user identifier is identified within the ownership data associated with the requested data element, populating one or more user interface data elements of the user interface with the requested data element; upon determining that the requesting user identifier is not identified within the ownership data associated with the requested data element, transmitting an access request notification to a user computing entity associated with a user identifier included within the ownership data of the requested data element; and upon receipt of an approval response from the user computing entity associated with the user identifier included within the ownership data of the requested data element, populating one or more user interface data elements of the user interface with the requested data element.

In accordance with various embodiments, the one or more memory storage repositories store the one or more record data objects in one or more relational database tables, wherein each of the one or more data elements are reflected within corresponding entries of the database tables, and wherein the ownership data is reflected within entries associated with the one or more data elements. In various embodiments, the method further comprises receiving an ownership transfer request from a user computing entity for a specific data element of a record data object; determining a current owner of the specific data element; transmitting an ownership transfer request notification to a user computing entity associated with the current owner of the specific data element; and upon receipt of a transfer approval from the user computing entity associated with the current owner of the specific data element, updating ownership data associated with the specific data element. In certain embodiments, upon receipt of the ownership transfer request for the specific data element of the record data object: determining a current owner of the record data object; transmitting an ownership transfer request notification to a user computing entity associated with the current owner of the record data object associated with the specific data element; and upon receipt of the transfer approval from the user computing entity associated with the current owner of the specific data element and a second transfer approval from the user computing entity associated with the current owner of the record data object, updating ownership data associated with the specific data element. In various embodiments, the method further comprises receiving a new data element from a user computing entity, wherein the new data element has corresponding metadata identifying the user computing entity; based at least in part on the metadata, identifying a record data object corresponding to the data element; and based at least in part on the identified record data object corresponding to the data element and the metadata, identifying ownership data corresponding with the new data element.

Various embodiments are directed to a computer program product comprising a non-transitory computer readable medium having computer program instructions stored therein, the computer program instructions when executed by a processor, cause the processor to: store, within one or more memory storage repositories, one or more record data objects each comprising a plurality of data elements, wherein each of the one or more record data objects comprises access data for each data element stored therein, and wherein the access data for each data element has associated ownership data identifying access credentials of the data element and wherein the record data object comprises a first data element identifying first access credentials associated with a first user identifier and a second data element identifying second access credentials associated with a second user identifier; receive a record data object access request for a particular record data object, wherein the record data object access request is associated with a requesting user identifier; retrieve access data associated with the particular record data object; generate a user interface for the record data object by: identifying one or more authorized data elements from the one or more data elements stored within the particular record data object, wherein the one or more authorized data elements have associated ownership data identifying the requesting user identifier; and populating one or more user interface data elements of the user interface with the one or more authorized data elements.

In certain embodiments, the record data object access request identifies a requested data element of the particular record data object, and wherein the computer program instructions when executed by a processor, cause the processor to further: determine whether the requesting user identifier is identified within the ownership data associated with the requested data element; upon determining that the requesting user identifier is identified within the ownership data associated with the requested data element, populate one or more user interface data elements of the user interface with the requested data element; upon determining that the requesting user identifier is not identified within the ownership data associated with the requested data element, transmit an access request notification to a user computing entity associated with a user identifier included within the ownership data of the requested data element; and upon receipt of an approval response from the user computing entity associated with the user identifier included within the ownership data of the requested data element, populate one or more user interface data elements of the user interface with the requested data element.

In various embodiments, the one or more memory storage repositories store the one or more record data objects in one or more relational database tables, wherein each of the one or more data elements are reflected within corresponding entries of the database tables, and wherein the ownership data is reflected within entries associated with the one or more data elements. In certain embodiments, the computer program instructions when executed by a processor, cause the processor to further: receive an ownership transfer request from a user computing entity for a specific data element of a record data object; determine a current owner of the specific data element; transmit an ownership transfer request notification to a user computing entity associated with the current owner of the specific data element; and upon receipt of a transfer approval from the user computing entity associated with the current owner of the specific data element, update ownership data associated with the specific data element. In certain embodiments, the computer program instructions when executed by a processor, cause the processor to further, upon receipt of the ownership transfer request for the specific data element of the record data object: determine a current owner of the record data object; transmit an ownership transfer request notification to a user computing entity associated with the current owner of the record data object associated with the specific data element; and upon receipt of the transfer approval from the user computing entity associated with the current owner of the specific data element and a second transfer approval from the user computing entity associated with the current owner of the record data object, update ownership data associated with the specific data element. In various embodiments, the computer program instructions when executed by a processor, cause the processor to further: receive a new data element from a user computing entity, wherein the new data element has corresponding metadata identifying the user computing entity; based at least in part on the metadata, identify a record data object corresponding to the data element; and based at least in part on the identified record data object corresponding to the data element and the metadata, identify ownership data corresponding with the new data element.

BRIEF DESCRIPTION OF THE SEVERAL VIEWS OF THE DRAWINGS

Reference will now be made to the accompanying drawings, which are not necessarily drawn to scale, and wherein:

FIG. 1 is a diagram of a system that can be used in conjunction with various embodiments of the present invention;

DETAILED DESCRIPTION

Figure 2A:
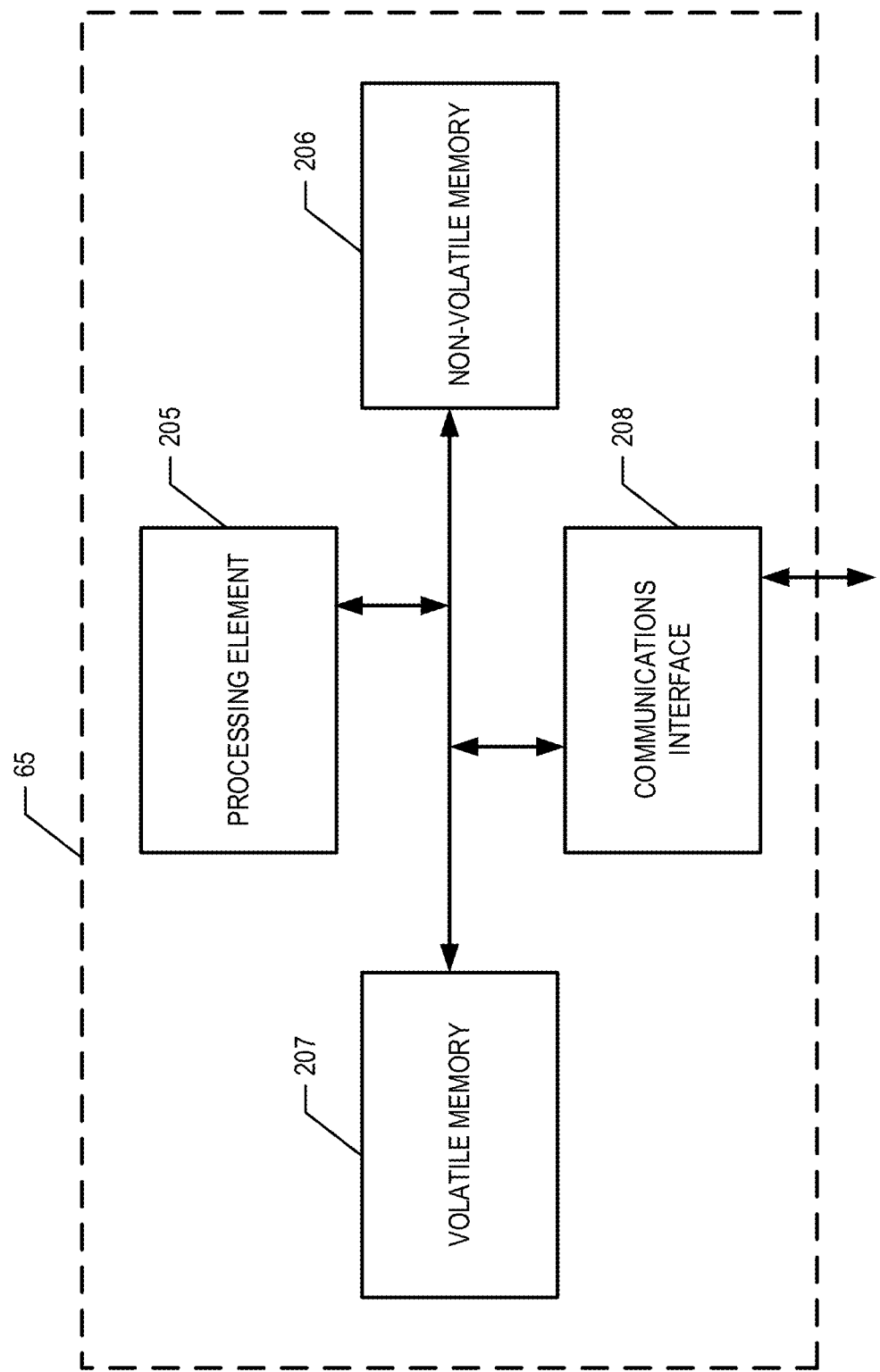
FIG. 2A is a schematic of a data management computing entity in accordance with certain embodiments of the present invention.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

I. Computer Program Products, Methods, and Computing Entities

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magneto resistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

FIG. 1 provides an illustration of a system 100 that can be used in conjunction with various embodiments of the present invention. As shown in FIG. 1, the system 100 may comprise one or more data management computing entities 65, one or more user computing entities 30 (e.g., which may encompass handheld computing devices, laptop computing devices, desktop computing devices, and/or one or more Internet of Things (IoT) devices, such as wearable devices, medical devices (e.g., Continuous positive airway pressure (CPAP) machines), and/or the like, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Data Management Computing Entity FIG. 2A provides a schematic of a data management computing entity 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the data management computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the data management computing entity 65 may communicate with other computing entities, one or more user computing entities 30, and/or the like.

As shown in FIG. 2A, in one embodiment, the data management computing entity 65 may include or be in communication with one or more processing elements 205 (also referred to as processors, processing circuitry, and/or similar terms used herein interchangeably) that communicate with other elements within the data management computing entity 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the data management computing entity 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, metadata repositories database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 (e.g., metadata repository) may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the system may be stored. As a person of ordinary skill in the art would recognize, the information/data required for the operation of the system may also be partially stored in the cloud data storage system and partially stored in a locally maintained data storage system.

Figure 2B:
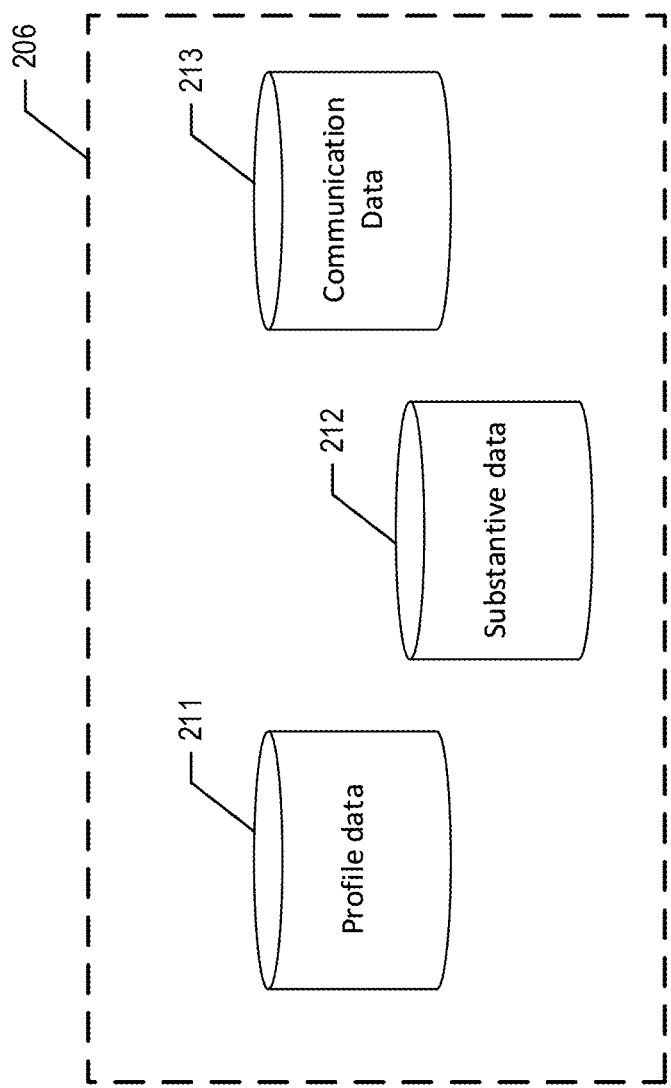
FIG. 2B is a schematic representation of a memory media storing a plurality of data assets.

Memory media 206 (e.g., metadata repository) may include information/data accessed and stored by the system to facilitate the operations of the system. More specifically, memory media 206 may encompass one or more data stores configured to store information/data usable in certain embodiments. For example, as shown in FIG. 2B, the memory media 206 may be embodied as one or more database storage areas (e.g., within a single centralized location or distributed among a plurality of disparate storage locations), and may comprise a plurality of data storage repositories, such as profile data storage area 211 (e.g., configured for storing data indicative of patient, provider, and/or other profiles as discussed herein), a substantive data storage area 212 (e.g., storing data provided for storage therein and associated metadata), a communication data storage area 213 (e.g., configured for storing data utilized for establishing and/or maintaining communication channels with one or more other computing entities and/or data indicative of appropriate communication interfaces to be utilized for communicating data to be provided to and/or received from one or more other computing entities). Data stored within such data repositories may be utilized during operation of various embodiments as discussed herein.

In one embodiment, the data management computing entity 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the data management computing entity 65 with the assistance of the processing element 205 and operating system.

As indicated, in one embodiment, the data management computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the data management computing entity 65 may communicate with computing entities or communication interfaces of other computing entities, user computing entities 30, and/or the like. In this regard, the data management computing entity 65 may access various data assets.

As indicated, in one embodiment, the data management computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data management computing entity 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The data management computing entity 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), Hypertext Markup Language (HTML), and/or the like.

As will be appreciated, one or more of the data management computing entity's components may be located remotely from other data management computing entity 65 components, such as in a distributed system. Furthermore, one or more of the components may be aggregated and additional components performing functions described herein may be included in the data management computing entity 65. Thus, the data management computing entity 65 can be adapted to accommodate a variety of needs and circumstances.

b. Exemplary User Computing Entity

Figure 3:
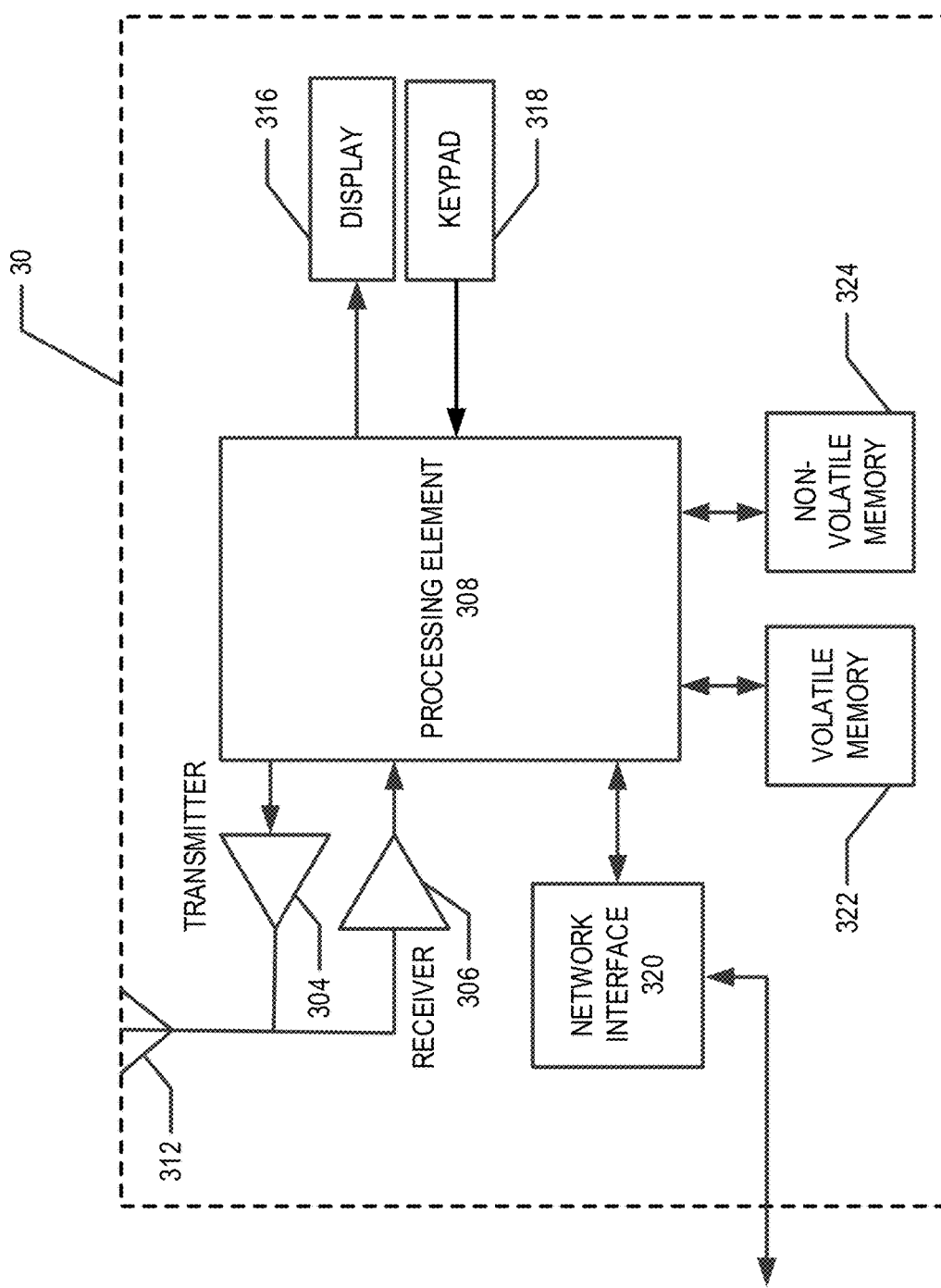
FIG. 3 is a schematic of a user computing entity in accordance with certain embodiments of the present invention.

FIG. 3 provides an illustrative schematic representative of user computing entity 30 that can be used in conjunction with embodiments of the present invention. As will be recognized, the user computing entity 30 may be operated by an agent and include components and features similar to those described in conjunction with the data management computing entity 65. Further, as shown in FIG. 3, the user computing entity 30 may include additional components and features. For example, the user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a data management computing entity 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface 1100 comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the data management computing entity 65. The user input interface can comprise any of a number of devices allowing the user computing entity 30 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. Exemplary System Operation

Details regarding various embodiments are described with respect to FIGS. 4-10C herein.

The process of predicting and diagnosing medical events increasingly relies on heterogeneous data generated and/or stored via a variety of data sources, including classical clinical records, genomic data, and several exogenous data sources, such as wearable devices (e.g., wearable fitness trackers, wearable computing devices, wearable sensors, and/or the like), ambient sensors in homes, vehicles, and offices, public data sources indicating pollution levels and other community-wide environmental exposures. Under existing technologies, collection and use of such data, and generation of corresponding insights, is primarily ad hoc and anecdotal, although emerging machine learning and other multi-data source diagnoses techniques are creating a need for data storage systems and methods that appropriately preserves the privacy and ownership rights associated with each piece of data while enabling access to such data to enable usage of emerging diagnosis techniques.

Accordingly, certain embodiments provide solutions to ownership origination and identification issues for individual portions of data within composite health records, specifically by identifying owner and data segment origins. As discussed herein, the owner of a data element within a health record is enabled to determine who has access to that element. Such concepts may be provided and/or applied via any of a variety of health records and/or data types, such as electronic medical records (EMRs), electronic health records (EHRs), individual health records (IHRs), and/or the like. As broad examples, diverse data relating to clinical, environmental, genetic, and/or other health-related factors may be aggregated to use the principles described herein. Such concepts may be utilized with cloud-based data storage platforms, individually-owned data repositories, distributed data storage systems, and/or the like. Moreover, although the following discussion focuses on the usage of various embodiments within the healthcare data storage context, it should be understood that certain embodiments may be utilized in any of a variety of data storage and/or retrieval contexts.

a. Overview

Various embodiments are directed to systems and methods for determining a source of data to be stored within a data storage environment (such as a centralized data storage environment or a distributed data storage environment) and for attributing and/or modifying data ownership attributes of individual data elements within a composite record data object to provide access control functionality to the individual data owners, thereby enabling generation of a composite user interface for a particular record data object comprising data elements each having differing data ownership attributes. A record data object as discussed in accordance with certain embodiments herein encompasses one or more database entries, with each database entry comprising one or more data elements. Moreover, as discussed herein, those data elements may comprise or may otherwise be associated with metadata that may be utilized to identify a source of the generation of the data elements (data elements within a record data object may be generated via a plurality of data sources) and/or to identify ownership of the data elements.

In accordance with certain embodiments, systems and methods utilize metadata accompanying data elements transmitted for storage within the data storage environment to attribute initial ownership to each data element, for example, utilizing a rule engine correlating various metadata elements with initial ownership. Specifically, systems and methods may determine source data within the metadata associated with a data transmission (e.g., upon receipt of the data at a memory storage repository, or after receipt of the data at a memory storage repository), and may utilize rules correlating the source data with ownership for each data element. In accordance with certain embodiments, ownership may be utilized by various systems to provide access and/or access levels to certain data (e.g., read-only access, read/write access, transfer access, and/or the like).

Moreover, through automated or at least partially manual interaction with the data elements, ownership of specific data elements may be updated and/or reassigned to additional users/systems/computing entities, for example, by updating ownership metadata stored with each data element. In certain embodiments, various systems may be configured to provide a notification to a designated owner (via any of a variety of communication channels) upon receipt of a request for ownership change for a data element. Upon receipt of an approval from the designated owner, the ownership data associated with the data element may be updated to reflect the changed ownership.

The system may provide composite data user interfaces comprising elements of a record data object for viewing by various users. The content of the user interface may be determined based at least in part on ownership data corresponding with each data element. Accordingly, the contents of the user interface may be constructed in real-time, based at least in part on the identity of the user (indicated by a corresponding user identifier) and ownership data indicating whether the user is an owner of/has access to each data element. Those data elements determined to be unowned by the user are not included within the generated user interface.

1. Technical Problem

Data stored within data storage repositories as cohesive data objects or otherwise associated with data objects are generally provided with common ownership and/or access rules. In other words, access to all individual data elements of a record data object are governed by a common set of access rules or other security measures. Accordingly, when assembling these record data objects comprising a plurality of individual data elements, data collectors must ensure that all data contributors are satisfied with rules and/or strategies utilized for determining when access is granted to the entire record data object. Existing systems and methods are incapable of providing only select data elements to particular users based at least in part on existing data ownership and/or access permissions for those individuals.

2. Technical Solution

Various embodiments provide a data storage structure and associated methodology for maintaining individualized data ownership rights and/or data access permissions for individual data elements within a collected record data object. Under such an organizational system, access to data within a single record data object may be managed by a plurality of data owners, such that access to data within a record data object may appear differently for different users, depending at least in part on ownership attributes and/or access permissions reflected within the data storage structure for the particular data viewer.

b. Data Receipt

In certain embodiments, the data management computing entity 65 is configured to analyze the origin of newly generated data elements (or data modifying existing data elements) as those data elements are provided to (or modified within) a data storage repository. However, it should be understood that the data management computing entity 65 may be configured to perform analysis of the origin of newly generated (or newly modified) data elements at any time, such as an instance after the data elements are already stored within a corresponding data repository. As an example, the following processes for determining the origin of data may be performed as a portion of a data receipt process and before storing the data element within a data storage repository. However, in other embodiments, such as certain example distributed data storage configurations, the origin of data may not be determined initially upon storage of the data within a data storage repository, such as an edge data storage repository in communication via a network with the data management computing entity 65. Under such a configuration, for example, the origin of data elements may be determined later, such as upon a next connection (chronologically next connection) between the edge data storage repository and the data management computing entity 65. Accordingly, modules, logic, rule engines, models, and/or the like utilized during data ownership attribution (and/or reassignment) processes need not be stored separately on each distributed data storage repository.

Figure 4:
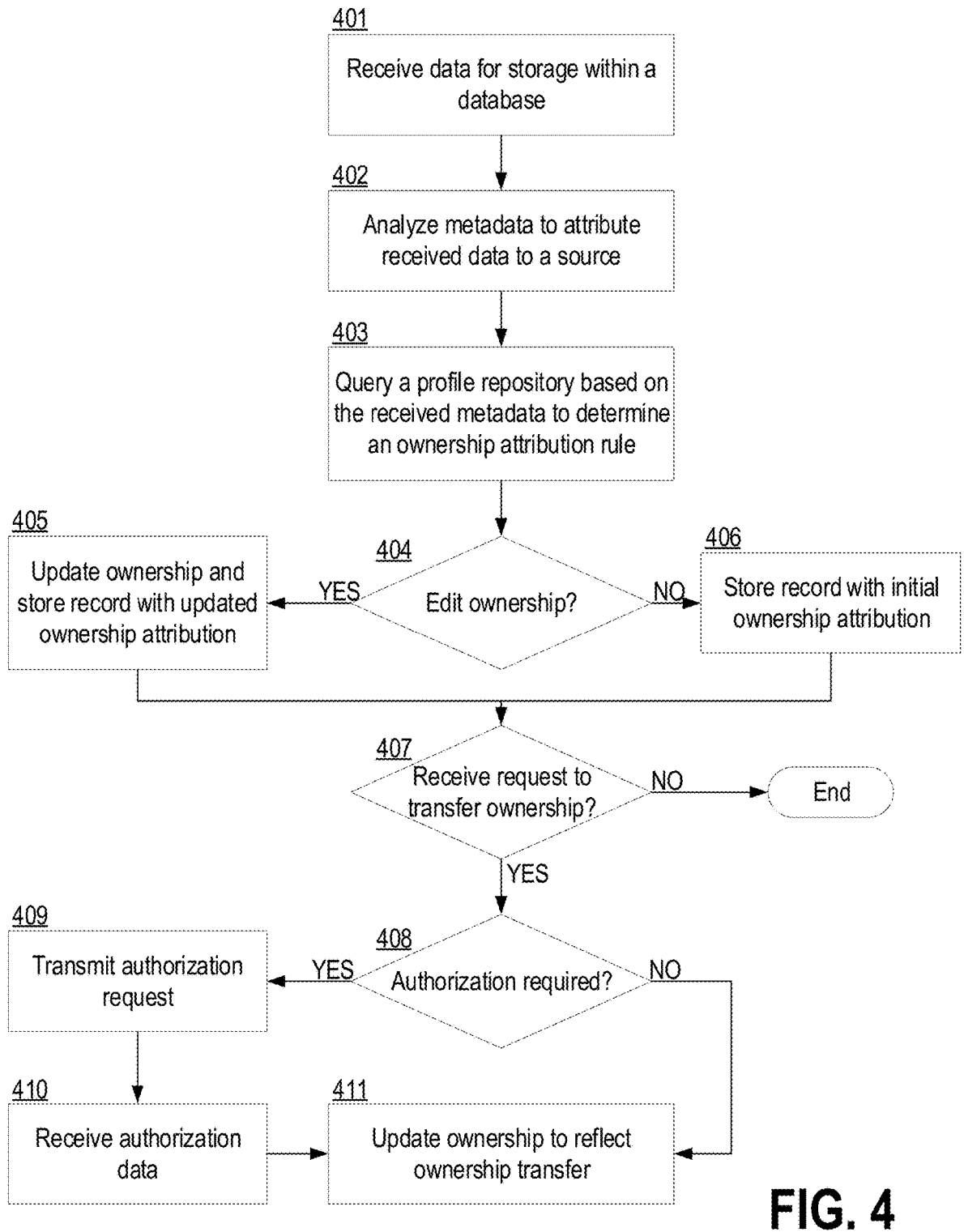
FIG. 4 is a flowchart illustrating an example process for intaking new data in accordance with certain embodiments.

With reference now to FIG. 4, which is a flowchart illustrating various processes associated with certain embodiments, data is received for storage within a data storage repository as reflected within Block 401 of FIG. 4. As discussed herein, the data embodying individual data elements for inclusion within a complete record data object may take many forms. For example, such data may be traditional medial records encompassing physician notes, diagnoses, prescriptions, data regarding hospital admissions, data regarding family history, data regarding physical characteristics of a patient (e.g., height, weight, sex, ethnicity, and/or the like), data embodying particular data elements of a record data object may also encompass data generated by various sensors associated with a particular patient, such as wearable sensors (e.g., body temperature sensors, pulse sensors, blood oxygen sensors, and/or the like), location sensors associated with a patient (e.g., a location sensor within a wearable device, a location sensor within a mobile device, altimeters within a wearable device, and/or the like), ambient sensors (e.g., ambient temperature sensors within a room, ambient temperature sensors within a home, ambient temperature sensors within a vehicle, and/or the like), data may also encompass manually-provided (e.g., by a patient, a physician, a guardian, and/or the like) data, such as data indicative of various social determinants of health (e.g., education level, income level, residential information, neighborhood information, and/or the like), and/or the like. Moreover, the data may be provided directly from generating devices (e.g., directly from a sensor device) or indirectly from a data management system associated with a generating device (e.g., from a cloud-based service managing and/or storing data associated with a sensing device).

The data may be received via appropriate application program interfaces (e.g., APIs) configured to map specific metadata elements to various known fields of the data management computing entity 65 to enable various analysis as discussed herein. Data may be received via any of a variety of communication protocols and may be received in any of a variety of formats. It should be understood that record data objects need not contain uniform data types (e.g., not all data elements must encompass data stored within a common file type). Indeed, the data management computing entity 65 need not have the capability to read the data to be managed, and accordingly the data management computing entity 65 is usable with any of a variety of future-developed data formats.

In other embodiments, data may be received in response to queries/requests generated by the data management computing entity 65, for example, to populate data into a record data object from a known data source.

It should be understood that the data encompassed within an individual data element may comprise raw data (e.g., individual sensor readings from a wearable device; textual data entries of a medical record; images of physician notes; and/or the like) and/or interpreted data (e.g., average body temperature measurements from a period of time as determined by a wearable device; ambient temperature data deemed relevant to a particular patient based at least in part on a known location of various ambient temperature sensors and a monitored location of the patient; OCR data generated based at least in part on images of physician notes; and/or the like).

As discussed herein, receipt of data may additionally comprise receipt of metadata (encompassing a plurality of individual metadata elements) corresponding with the data to be provided as a data element. The metadata may comprise time of generation metadata (e.g., a time/date stamp), time of receipt metadata (e.g., a time/date stamp), an IP address associated with the data source, a serial number associated with the data source, a device type associated with the data source (e.g., identifying a device type specifically by model, such as a Google Nest, an Apple iPhone, and/or the like; or identifying a device type generically, such as a temperature sensor, a humidity sensor, and/or the like), metadata indicative of device ownership, metadata indicative of device possession (e.g., indicating the possessor of a rented/borrowed device), location metadata indicative of the location of data generation (e.g., a street address, GPS coordinates, a user-provided location identifier (e.g., House 1 master bathroom), and/or the like), communication metadata indicative of a communication protocol utilized for providing the data to the data storage repository, and/or the like. In certain embodiments, the metadata may additionally comprise a user identifier (if the data is provided for storage via a data communication protocol accessible via a log-in to one or more data storage systems and/or data management systems (e.g., the data management computing entity 65, an EMR system, and/or the like). In various embodiments, metadata elements may be embodied as user-provided input to be associated with a data element. For example, the user-provided metadata may identify an owner of the data, may identify a record data object for the data, and/or the like.

Upon receipt at a data storage repository, the data and underlying metadata may be associated with one another (e.g., within a relational database, via data tables, and/or the like). Moreover, for data to be associated with an overarching record data object, metadata (or portions of the substantive data) indicating a record data object for associating the data element therewith.

Figure 5:
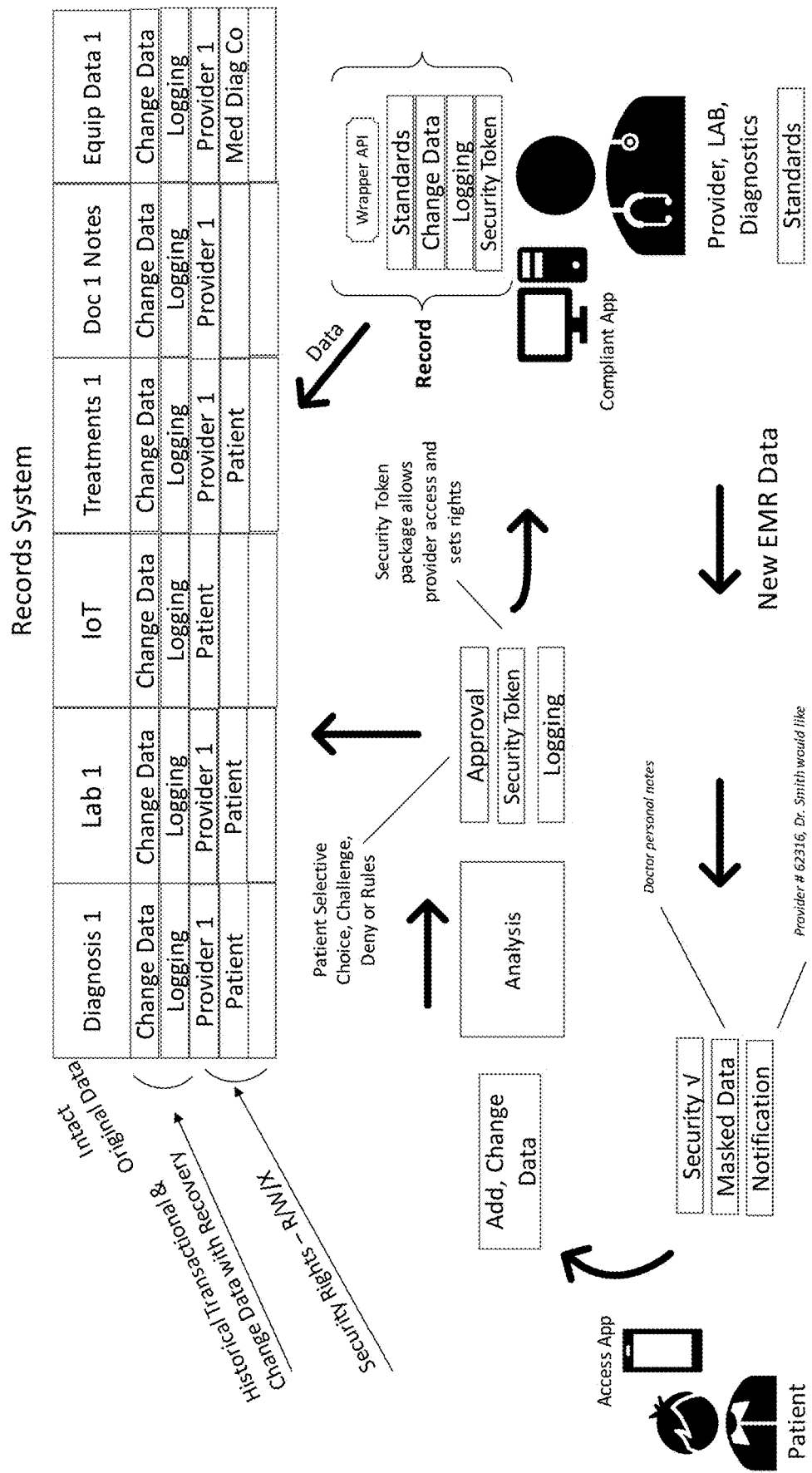
FIG. 5 is a schematic flow diagram illustrating an example process for intaking new data for attribution to an existing record in accordance with certain embodiments.

As illustrated in the specific example of FIG. 5, new data may encompass new EMR data generated by a healthcare provider, lab, diagnostics device, and/or the like. In certain embodiments, the data may be provided for storage within a data storage repository via a communication protocol associated with a specific computing program (an "app") executing on a user computing entity 30 associated with the provider. As just one example, the app may encompass an EMR management application executing on the provider's user computing entity 30, although it should be understood that any of a variety of communication protocols that may be associated with various applications executing on a user computing entity 30.

As specifically shown in the example of FIG. 5, the data may be provided directly from a source computing entity (e.g., a user computing entity 30 associated with the provider). This data may be provided via a specially configured app (e.g., an app associated with the user's EMR system) communicating via a communication protocol and providing data that may be prepared for storage within the data storage repository in accordance with an API (e.g., the illustrated wrapper API), which may be configured to enable capture and storage of various metadata as illustrated in FIG. 5 (e.g., such as change data, logging, security tokens, and/or the like).

However, as additionally illustrated in FIG. 5, certain embodiments may be configured to enable record data object owner control over data that may be stored within the record data object (e.g., whether the data encompasses new data elements requested to be stored within the record data object or changes to existing data elements previously stored within the record data object). As shown in FIG. 5, upon the generation of new data elements (or modifications to existing data elements) for storage within a record data object, the data management computing entity 65 may be configured to identify a record data object for which the new data is to be attributed and to identify a record data object owner for the identified record data object (e.g., by querying a database of the data management computing entity 65). The data management computing entity 65 may then provide a data storage request notification to the record data object owner, which may indicate explicitly what data is requested to be stored in association with the identified record data object. However, it should be understood that in certain embodiments, the data storage request notification need not comprise the exact content of the data requested to be stored, and may instead comprise a summary (e.g., an automatically generated summary, such as an identification of the data type) of the data requested to be stored in the record data object. The record data object owner may be provided with an ability to provide user input (e.g., directly to the data management computing entity 65, such as by providing user input to an electronic notification, or indirectly, such as by instructing a proxy or another user (e.g., via phone, mail, and/or the like) to provide an identification of approval of storage of the requested data) approving or denying storage of the requested data. Data indicating the approval (or denial) is provided to the data management computing entity 65. Upon receipt of approval, the data management computing entity 65 accepts the data provided from the data source for storage within the record data object. Upon receipt of a denial, the data management computing entity 65 provides a notification to the data source indicating that storage of the data was rejected.

c. Initial Data Source Attribution

Once data elements are provided for storage within a data storage repository, a source of the data elements may be determined as a part of determining initial ownership attribution of the data elements. As discussed in greater detail herein, other data/metadata may be utilized in establishing initial data ownership, such as metadata indicative of relationships between data elements and overarching record data objects, as well as any default ownership data (if applicable) associated with the record data object.

Data ownership may be determined and/or indicated in reference to one or more user profiles stored within and/or in association with the data management computing entity 65. A single user profile may be attributed to each of a plurality of individuals, such as patients, care providers, relatives, and/or the like. In other embodiments, a single individual may be associated with a plurality of user profiles each corresponding to a different capacity of the individual (e.g., a physician may have his/her own "patient" user profile (including the physician's own personal health data), a physician user profile (enabling access to other individual's health data in a professional capacity), a healthcare entity user profile corresponding to the physician's employer hospital/care facility, and/or the like. However, certain embodiments may be configured for identifying duplicative user profiles during one or more profile cleanup procedures (e.g., so as to avoid generation of a plurality of "patient" profiles for a single individual), such as by identifying duplicate records each containing identical data that is unique to a particular individual, by utilizing fuzzy logic to identify misspelled user data that would otherwise be identified as unique record data objects, to identify record data objects stored in a plurality of data storage areas that all correlate with a single individual, and/or the like.

User profiles corresponding with a patient may comprise identifying data of the patient, such as the patient's name and/or one or more unique identifiers (e.g., social security number). In certain embodiments, a patient profile may additionally comprise a unique user name (and corresponding password) that may be used by the patient to log-in to the data management computing entity 65 to provide various preferences, to respond to prompts (as discussed herein), and/or the like. In certain embodiments, the user profiles may additionally comprise biographical data regarding the user (e.g., date of birth, an identification of related family members (which may enable links with other user profiles), height, weight, ethnicity, sex, and/or the like), health data regarding the user (e.g., allergies, conditions, medications, family medical history, and/or the like). It should be understood that any unique data contained within the user profile may be utilized in certain embodiments for linking the user profile with ownership and/or access privileges corresponding with a particular piece of data. Moreover, the patient user profile may be utilized for establishing ownership or otherwise linking the patient user profile with an overarching medical record data object (comprising a plurality of individual data elements), with such links being utilized for establishing at least a portion of data ownership over one or more data elements within the record data object as discussed in greater detail herein.

Similarly, user profiles corresponding with a provider (or other user) may comprise identifying data of the provider (or other user), such as the provider's name and/or one or more unique identifiers and/or a user name (and corresponding password). Unique data provided within the user profile corresponding to the provider (or other user) may be utilized for association with particular data elements of a record data object to establish ownership and/or access privileges associated with the particular data element.

In various embodiments, the user profiles may additionally comprise data indicative of various data sources that may be associated with the individual, for attributing ownership and/or access privileges to data elements generated and/or provided by those data sources. As non-limiting examples, a user profile may comprise data identifying a device serial number (or other unique device identifier), a device location (e.g., GPS coordinates, local area network connectivity, and/or the like), a device type, and/or the like, which may identify various data sources to be associated with the user identifier. Such user profile content may be applicable to any of a variety of user profiles (e.g., patient user profiles, provider user profiles, other user profiles, and/or the like).

In certain embodiments, a user profile may be associated with and/or may comprise a record data object, thereby establishing an ownership connection between the entire record data object and a particular user profile. As just one example, medical records associated with a patient may be stored within a record data object that is stored as a part of (or otherwise associated with) the patient's user profile. As discussed herein, ownership over a particular record data object may not provide access privileges to all data elements stored within the record data object, however ownership over the record data object may provide some amount of control (e.g., approval/denial privileges) over data element transfers, data element access requests, data element ownership changes, and/or the like. Indeed, the owner of a particular record data object may not have viewership access over all data elements—even those for which the record data object owner has privileges for approving or denying data element transfers, data element access requests, data element ownership changes, and/or the like, the data management computing entity 65 may provide the record data object owner with the ability to approve or reject such changes to data elements without the record data object owner having access to those data elements.

The user profiles may additionally comprise data indicative of desired communication protocols to be utilized for contacting the user. Such data may be stored together with communication data to be utilized for communicating with the user (e.g., an email address, a user name, a phone number, a cellular phone number, a social media contact name, a mailing address, and/or the like). For example, communications may be provided via a computer program operable on a user computing entity 30 associated with the user. In such examples, the user may be required to sign-in to the computer program (e.g., using a user name and corresponding password) to access notifications. As another example, communications may be provided via an electronic communication protocol (e.g., email, instant message, text message, multimedia message, and/or the like), which may require the user to sign in (e.g., using a user name and password) to respond to any prompts provided in the notification. However, in other embodiments, the user may respond simply by submitting a response to the electronic notification (e.g., a responsive email, a responsive text message, and/or the like). As yet another example, communications may be provided via physical mailing, which may request the user to log-in to an electronic website to provide a response and/or to mail back a response card (or other portion) of the mailed communication to respond. Accordingly, although a user profile may be stored electronically for a particular user, such users may not be required to access (or have access) to electronic methodologies for communication to respond to notifications. In such embodiments, a user may designate a user proxy (e.g., a relative, a caretaker, a guardian, a physician, and/or the like) with appropriate authority to maintain, update, and/or establish data within the user profile on behalf of the user. The user proxy may be established by a link to another user profile (e.g., to a provider's user profile) which identifies proxy access levels provided to the identified proxy user identifier on behalf of the providing user identifier. As an example, the link may be embodied as proxy data indicating that a particular patient (having a corresponding user profile) has given consent to the patient's healthcare provider (having a corresponding user profile) to manage a record data object (or one or more data elements) owned by the particular patient. In certain embodiments, the proxy data may indicate that the user has provided complete proxy privileges to the proxy user identifier. In other embodiments, the proxy data may indicate that the user has provided partial proxy privileges (e.g., only providing the proxy with the capability to act on behalf of the particular user for certain actions) to the proxy user identifier.

As discussed in greater detail herein, various user profiles may additionally comprise one or more rules that may be implemented by a rules engine for attributing ownership and/or data access permissions to one or more user profiles. For example, such rules may indicate that data generated by a particular device associated with the user should be attributed to the user (and corresponding user profile) as well as a related physician (and corresponding user profile). Other rules that may be stored within one or more user profiles are discussed in greater detail herein.

In certain embodiments, a portion of determining a source of data comprises analyzing metadata received with the data for storage, as indicated at Block 402 of FIG. 4, to determine a data source. In certain instances, the analysis of the metadata to determine a data source may be a single-step process, such as in embodiments wherein the source of the data is explicitly defined within the metadata. For example, physician notes that are manually provided via user input to a user computing entity 30 and which are ultimately provided for storage within a data storage repository may comprise data identifying the physician who entered the notes, a healthcare entity associated with the physician, the patient for which the notes are provided, and/or the like. Moreover, the metadata may explicitly indicate source data (e.g., via tags associated with at least a portion of the metadata indicating which piece of metadata is indicative of the source of the corresponding data). In certain embodiments, the data management computing entity 65 may be configured to provide a high (e.g., a highest-possible) confidence rating to a determination of a source for such a configuration. Moreover, the metadata indicating a source may comprise and/or may be associated with at least one user identifier at the data management computing entity 65 so as to attribute the source of data to a user profile.

However, in other embodiments, determining a data source may be a multi-step process, and/or may have a lower confidence rating associated with the determination of a source. In other embodiments, attributing a source to data may comprise attributing multiple sources to the same data, for example, where the underlying data is applicable to a plurality of individuals.

As just one example, upon receipt of data (and corresponding metadata) for storage within a data storage repository associated with the data management computing entity 65, the data management computing entity 65 may analyze the received metadata to identify one or more pieces of metadata that may be utilized to determine a source of the data. The identification of one or more pieces of metadata that may be indicative of a data source may be determined through any of a variety of methods, such as rule-based determinations of certain data that may be utilized to attribute ownership, trial-and-error searching strategies based at least in part on all or a portion of the metadata, machine-learning based models that identify a likelihood of using a piece of metadata to successfully identify ownership, and/or the like. For example, the data management computing entity 65 may query one or more user profiles based at least in part on at least one piece of metadata received with the data for storage to identify one or more user profiles indicating that the metadata is associated with the user profiles. For example, a piece of metadata associated with the data may comprise a mobile device serial number indicative of the mobile device utilized to generate the data. Querying the plurality of user profiles may thus comprise determining whether any of the user profiles comprise data identifying the same mobile device serial number (e.g., which may be indicative of the user device being owned by the individual associated with the user profile). It should be understood that the data within the user profile may be manually populated or may be automatically attributed to the user profile (e.g., via machine-learning techniques identifying patterns of attribution between a particular piece of metadata and the user profile).

In various embodiments, the data management computing entity 65 may be configured to query the user profiles based at least in part on a plurality of pieces of metadata associated with the data provided for storage, for example, as a part of determining a confidence rating to be associated with the ownership attribution. As just one example, a higher number of identified matches between metadata and a single user profile may result in a higher confidence rating of the attribution. However, it should be understood that other methodologies for determining a confidence rating may be utilized, such as by assigning weights to various pieces of metadata (e.g., determining a match between a user identifier associated with the provided data and a user profile may receive a higher weight, and therefore a higher confidence rating, than correlating a serial number of an ambient senor IoT device (e.g., a home thermostat) with a user profile).

Moreover, data may be attributed to a plurality of user profiles as a source in accordance with certain embodiments. For example, ambient sensor devices or other non-wearable IoT devices may provide data to be associated with a plurality of individuals (e.g., a plurality of residents of a single home encompassing the IoT sensor device), and accordingly in such embodiments the source of the data from the IoT sensor device may be attributed to a plurality of user profiles in the manner as discussed above.

In other embodiments, a particular device (and therefore metadata generated by the particular device) may be temporarily associated with a particular individual (and corresponding user profile). For example, devices that are rented by a particular individual, borrowed by a particular individual, and/or the like may be temporarily possessed by the particular individual, and accordingly any data generated during the particular individual's possession should be attributed to the particular individual, rather than the actual owner of the device. Accordingly, temporary possession of a device may be determined automatically or manually. In the latter configuration, an owner of the device (or a temporary possessor of the device) may provide user input data to the data management computing entity 65 indicating temporary possession of the device. In certain embodiments, one or more security measures may be provided to ensure that the possessor has actual possession of the device. For example, the data management computing entity 65 may be configured to transmit multi-factor authentication notifications to multiple devices (including the device for which temporary possession is to be established) to establish whether the identified possessor has actual possession over the device. It should be understood that any of a variety of methodologies may be utilized to establish actual possession of a device.

In certain embodiments actual possession may be determined automatically, for example, based at least in part on data and/or metadata generated by a plurality of devices, and a determined confidence level that may be established for possession of a particular device. For example, upon receipt of data indicating a location of a plurality of devices all associated with a particular user, the receipt of additional data from another device having a similar location may indicate that each of the devices are possessed by a common individual. Such location data may be utilized to establish a confidence rating indicative of a likelihood that the device is in the possession of the same user as the other devices. In certain embodiments, upon determining that a confidence level satisfies a threshold, the data generated by the device may be indicated as attributed to the user profile corresponding with a particular individual. However, if the confidence rating is below the threshold, one or more notifications may be generated and transmitted by the data management computing entity 65 to request manual confirmation of device possession (e.g., via one notification or a plurality of multi-factor authentication notifications to establish confirmation of possession with a defined level of confidence).

In certain embodiments, various embodiments are configured to retrieve publicly available data for association with one or more record data objects. This publicly available data may be stored within one more data elements that may be associated with a single record data object, or with a plurality of record data objects. In certain embodiments, a record data object (e.g., embodied in association with one or more data storage tables) may comprise one or more links or other relational references to data elements comprising publicly stored data for association with the record data object. In such embodiments, these public data elements may be indicated as owned by all user identifiers, thereby enabling access to the publicly available data by all users of the data storage repository. It should be understood that other ownership configurations may be provided in other embodiments for the publicly available data so as to provide universal access to the publicly available data (e.g., such that the publicly available data may be provided as a portion of a user interface generated for viewing of data associated with a particular record data object).

d. Data Storage and Ownership

As discussed herein, data may be stored in any of a variety of data storage repositories, such as a centralized data storage repository or one or more distributed data storage repositories. Data may be stored in one or more data tables, wherein individual data elements and individual metadata elements may be associated with a plurality of data table entries which may establish ownership, data access, and/or other characteristics of the data elements. Moreover, such data table entries may additionally relationally attribute the data element to a particular record data object, such as via storage within a single data table attributable to the record data object, storage within a data table and having table entries corresponding with the record data object, and/or the like. Furthermore, as discussed herein, the record data object may be further associated with one or more user profiles, thereby establishing ownership over the record data object (which may enable various permissions and/or other data management privileges, so as to enable the record data object owner to manage access to various data elements stored therein).

As mentioned herein, ownership and/or initial data access permissions may be established upon receipt of data for storage within a data storage repository, upon establishing a connection between a remote data storage repository and the data management computing system (e.g., after storing data within a corresponding data storage repository), and/or the like. In instances in which data is stored in remote data storage repositories, each data element may be stored within a data table configured for storing data ownership and/or data access credentials in association with the data element. Moreover, the data element may be stored with additional data within the data storage table identifying a record data object for which the data element is associated. Particularly in those embodiments in which the remote data storage repository is operable without connection with the data management computing entity 65, the remote data storage repository may be configured to store data elements within a data table with placeholder data regarding ownership and/or data access privileges until the data management computing entity 65 determines appropriate data for storage therein (e.g., after determining data ownership and/or data access privileges).

Data ownership for a data element may be automatically determined by the data management computing entity 65, for example, based at least in part on metadata associated with the data element and/or other characteristics of the data element. For example, with reference to Block 403 of FIG. 4, initial data ownership may be determined based at least in part on execution of a rules engine in association with the data management computing entity 65. As just one example, the data management computing entity 65 is configured to query one or more profiles identified as corresponding with the data element (e.g., based at least in part on determined relationships based at least in part on an attributed data source) to identify corresponding ownership and/or data access rules. The applicable rules may be retrieved from the appropriate user profiles and utilized for analyzing the data element to determine appropriate data ownership.

As just one example, one or more data ownership rules may establish that the user profile associated with the data source is to be identified as the initial owner of the data. This initial ownership rule may be universally applicable, or may be applicable to a subset of all generated data elements (e.g., data elements identified as originating from a particular device, from a particular user, and/or the like). As a specific example, for data elements determined to be generated by a device associated with a user profile that is also associated with the overall record data object (e.g., a patient user profile corresponding to the same patient's patent record data object), the data ownership rules may establish that data ownership is to be established with the user profile of the record data object.

As another non-limiting example, one or more data ownership rules may establish that the user profile associated with the data source and the user profile associated with the record data object are to be determined as dual owners of the data for data determined to be sourced from a data source not associated with the record data object. As a specific example, for patient data generated by a healthcare facility (e.g., lab test results), the data management computing entity 65 may be configured to establish the healthcare facility and the corresponding patient (through respective user profiles) as dual owners of the data.

As yet another example, data ownership rules may establish that ownership cannot be established (or modified) without approval of one or more users. Under such circumstances, data may be stored within a data storage repository, and ownership may be established subsequently, upon receipt of appropriate approvals from one or more users. In other embodiments, the data may be stored within a temporary cache until ownership is established, at which point the data may be transferred for storage within the data storage repository. As a specific example, data elements to be stored as a portion of a record data object may require approval of the owner of the record data object prior to establishing ownership of an individual data element. Such an example is illustrated in FIG. 5, in which a physician requests to provide data for storage in association with a patient record. Upon providing the data for storage, the data management computing entity 65 generates and provides a notification to the patient (e.g., provided in accordance with communication preferences as established within the patient's user profile) requesting approval for storage of the lab data within the patient's record (as shown, the lab data may encompass a single cohesive data element to be added to the patient's record data object which additionally comprises a "Diagnosis 1" data element, an IoT data element, a "Treatments 1" data element, a "Doc 1 Notes" data element, and an "Equip Data 1" data element, and requesting that the physician be given ownership access to the lab data stored within the patient's record data object. The patient may provide approval (or may deny) via appropriate methodologies as determined by the utilized communication channel, which causes the data management computing entity 65 to update the ownership data to be associated with the data element upon storage thereof in the data storage repository. In such embodiments, the patient may be provided with access to the lab data as a part of the notification and/or upon establishing at least partial ownership over the data upon storing the data elements within the data storage repository. However, it should be understood that for certain data elements for which approval of the patient is required prior to establishing data ownership, the patient may not be provided with access to the underlying content of the data element, and the patient may instead be provided with a summary of the underlying data element. As an example with reference to FIG. 5 (discussed in greater detail herein), the patient notification may indicate that the physician is seeking to store physician notes within the patient's record data object, for which physician-only ownership is requested (such that the patient cannot view the contents of the physician notes). Upon receipt of appropriate approval from the patient (or other record data object owner), the provider notes may be stored within the patient record data object together with data identifying the data element as solely owned by the physician.

Data ownership may also be established based at least in part on user data corresponding with a record data object. For example, data elements to be stored within a record data object corresponding with a minor (e.g., under the age of 18) may be indicated as owned by the minor's parent or legal guardian (through a corresponding user profile). Under such circumstances, upon receipt of a data element to be stored with a record data object of the minor, the data management computing entity 65 may retrieve corresponding data ownership rules, which may establish that ownership is dependent at least in part on the age of the record data object owner. Thus, the data management computing entity 65 may retrieve data stored within the user profile (e.g., biographic data) to determine how to establish ownership based at least in part on the data stored within the user profile. Under such configurations, ownership may be automatically reestablished upon identification of changes in relevant data stored within the user profile (e.g., upon the minor reaching the age of 18).

In certain embodiments, data ownership may be established based at least in part on characteristics of a device determined to be the source of the data element. As discussed above, possession of a device may be established via any of a variety of methodologies, such that possession of a device may be attributed to a particular individual, regardless of actual device ownership. Accordingly, data indicating possession of a particular device may be utilized to establish ownership of data generated by the device. For example, data generated by a wearable device owned by user A, but determined to be worn (and possessed) by user B may be identified as owned by user B upon attributing possession of the device to user B in accordance with the methodology as discussed above. It should be understood that other data ownership attribution rules may be applied to data upon determining that the generating device is possessed by user B (e.g., to share ownership of the data, to provide ownership to a guardian, and/or the like).

In certain embodiments, establishing data ownership may comprise establishing access privileges to be associated with one or more users. Access privileges may be assigned as read only access, write only access, read and write access, deletion access, transfer access, and/or the like. Data ownership may establish a highest level of data access, including, for example, read access, write access, deletion access and transfer access. However it should be understood that in certain embodiments data ownership may have lower access levels as required by certain embodiments. Other access levels may be provided to non-owners of the data, such as data viewer access levels, data write access levels, and/or the like. In certain embodiments, the data storage environment may identify one or more user identifiers having non-ownership access privileges to particular data elements.

e. Data Ownership Transfer

Over time, the ownership of various data elements within a record data object may be changed. Ownership changes may encompass additions of owners (e.g., changing a data element from a single owner to dual ownership), changing owners (e.g., changing from a first single owner to a second single owner or changing from a first dual owner to a second dual owner, and/or the like). For example, as illustrated at Blocks 404-406 of FIG. 4, ownership of data may be established upon storing the data within a data storage repository, for example, by determining whether any rules, requests (e.g., manual user-provided requests), and/or the like require changes to the initial ownership determination, as discussed above.

In certain embodiments, a change in ownership may comprise adding a new owner not otherwise indicated as having an ownership interest in any data elements stored within a record data object. In certain embodiments, such additions of data owners may be accomplished in response to an automated determination that a change in ownership is required (e.g., based at least in part on executing one or more rules by the rule engine analyzing metadata or other data associated with the data element). In certain embodiments, changes in ownership (and/or other changes in characteristics associated with a particular data element and/or data record) may be reflected within data stored within an immutable data storage structure (e.g., an immutable ledger), such as a blockchain data storage structure (e.g., a permissioned blockchain storage structure), wherein sequentially generated blocks may store data indicative of a current owner (and/or data indicative of access permissions) associated with a particular data element and/or a particular data record. Thus, as newly generated blocks are generated within the data storage structure, prior blocks remain unmodified, thereby providing an immutable record of all owners (including current and past owners) of a particular data element and/or a particular data record.

In other embodiments, addition of owners to a particular data element may be initiated by a manual request to add a user as an owner of the data element. Such requests may originate from a current owner (e.g., the initial owner) of the data element, or by non-owners seeking access to the data within the data element. As yet other embodiments, requests to add an owner may originate by a non-owner seeking to add another non-owner as an owner of the data element.

As just one example, a current owner may request to add another owner to a data element. Such a request may originate at a user computing entity 30 associated with the data owner, which may be provided to the data management computing entity 65. Because the request to add an owner originated from an owner of the data, no additional confirmations may be required in many circumstances. However, in those circumstances in which the requested addition of a new owner is provided by a co-owner of the data element, the data management computing entity 65 may be configured to generate and provide a notification requesting approval to add a new owner to other (non-requesting) co-owners of the data element. Moreover, in certain embodiments, the data management computing entity 65 may be further configured to generate and provide a notification to the new owner (e.g., by identifying communication preferences within a user profile associated with the new owner) indicating the new owner has ownership access rights associated with the data element. It should be understood that a similar process may be provided for providing other, non-ownership access privileges (e.g., viewership data access privileges) to non-owners of the data element.

Figure 6:
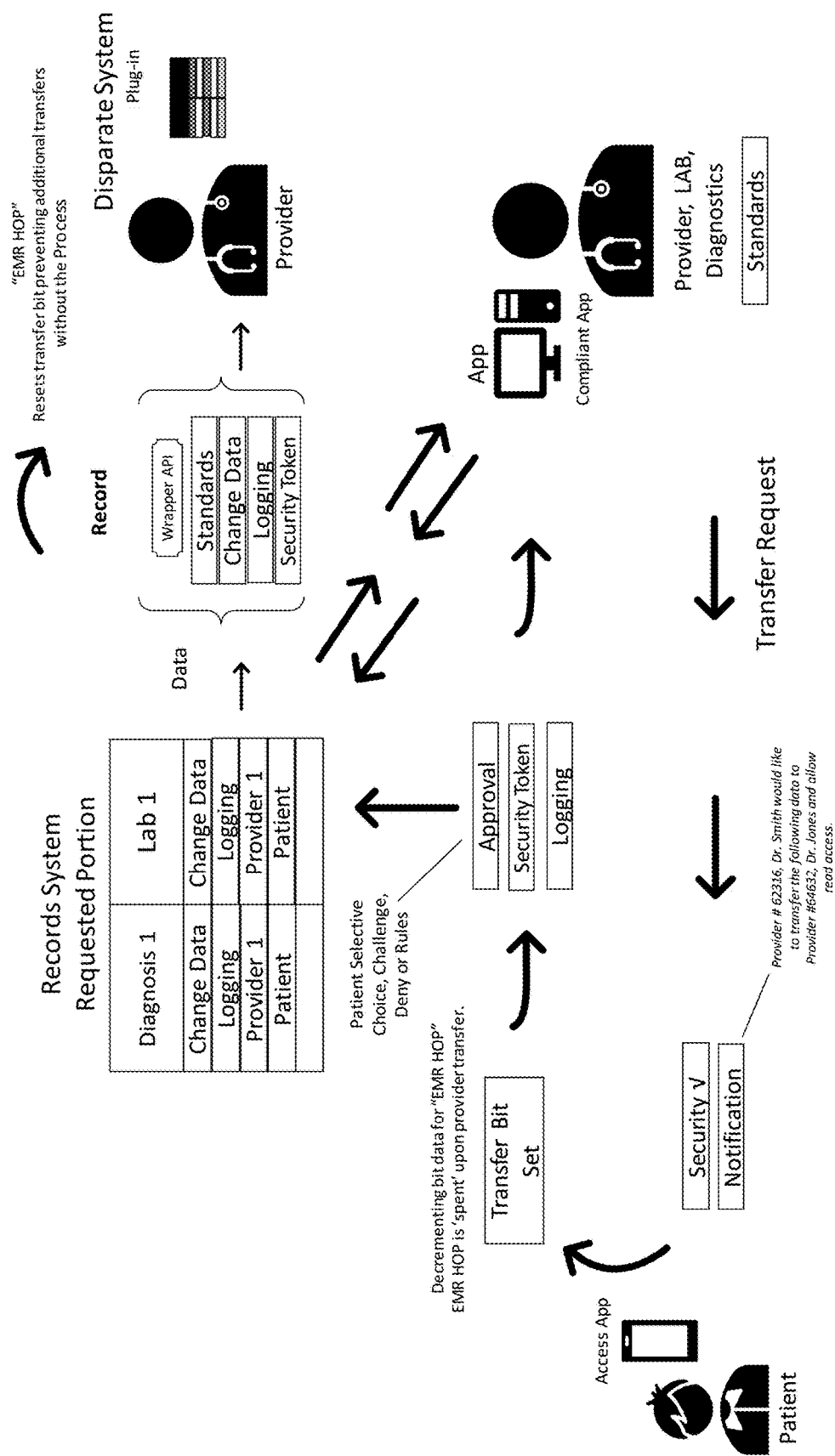
FIG. 6 is a schematic flow diagram illustrating an example process for transferring data ownership in accordance with certain embodiments.

FIG. 6 illustrates an example process for transferring ownership of a particular data element (e.g., "Diagnosis 1" data element and "Lab 1" data element) from a first provider ("Dr. Smith") to a second provider ("Dr. Jones"). As a specific example, such a data transfer may occur if Dr. Smith recommends that the patient see a specialist, specifically Dr. Jones. As shown in FIG. 6, the first provider may initiate a transfer request (e.g., via an app interfacing with the data management computing entity 65) identifying the particular data elements. The data management computing entity 65 may then identify a corresponding record data object owner, thereby providing a transfer request notification to the data owner (the patient). As shown, the transfer request notification includes a textual notification providing data indicative of the requesting user identifier, the intended recipient of the transfer, and identifying the particular data elements for which ownership is to be transferred. As shown, the data management computing entity 65 may be configured to utilize a transfer bit set configuration for executing the transfer, and in such configurations, the data management computing entity 65 may be incapable of executing the transfer until receipt of data indicative of an approval of the transfer from the record data object owner. In certain embodiments, the data indicative of the approval may be provided in the form of a token (e.g., a hashed data string representative of the content of at least a portion of the data transfer notification). The data management computing entity 65 may be configured to receive the token, to determine the authenticity of the token (e.g., via a key algorithm that may be utilized to generate a copy of the token based at least in part on known data utilized for generation of the token), and to exhaust the transfer bit set (e.g., by decrementing bit data associated with the transfer bit set based at least in part on the determined authenticity of the token) while simultaneously updating the ownership identifying data associated with the transferred data elements. In certain embodiments, the transferred data may be provided to the intended recipient (e.g., via an API interacting with applications executing at the intended recipient's user computing entity 30) and/or the intended recipient may receive a notification that the transferred data is available for access.

As another example, a non-owner may request access to one or more data elements (e.g., for himself/herself or a different non-owner). As a specific example, a physician may request access to data generated by a wearable device of a patient for himself/herself or for another colleague (e.g., a specialist). Because the non-owner does not have access to the data prior to the request, the data management computing entity 65 may be configured to provide information to the non-owner regarding the types of data elements included within the record data object, thereby enabling the non-owner to identify data for requesting access. In other embodiments, the data management computing entity 65 may not provide information regarding the type of data available, and therefore the non-owner may request access to any data elements (regardless of whether those data elements exist or not) or the non-owner may request access to all data elements. Upon receipt of such a data access request, the data management computing entity 65 may generate and provide a notification to the current owner(s) of the data element to request consent for adding a new owner. In certain embodiments, the notification may be configured to receive user input enabling the owner to modify the requested data elements (e.g., to add additional data elements, to remove data elements, and/or the like) so as to customize the data elements to which the non-owner is to be added as a new owner. Upon receipt of an approval to add the non-owner as an owner to one or more data elements, the data management computing entity 65 is configured to update the data entries associated with the data element to reflect the new ownership. It should be understood that similar processes may be utilized for providing other, non-ownership access (e.g., viewership access) to various data elements. Moreover, in certain embodiments, requests to add a new owner to various data elements may additionally require approval from the owner of the overall record data object, and accordingly the data management computing entity 65 may be configured to generate and transmit a notification to the owner of the record data object (if different from the owner of one or more data elements) to request user input indicative of approval to add an owner to one or more data elements included within the record data object.

As indicated at Blocks 407-411, updating ownership of a data element may additionally encompass processes for changing ownership (removing an existing owner to replace the existing owner with a new owner of the data element). If, as indicated at Block 407, no request to transfer ownership of a data element is received, the process ends, as indicated. However, upon receipt of a request to transfer ownership (e.g., from a current owner of a data element, from a current non-owner of a data element, and/or the like), the data management computing entity 65 may be configured to initiate a process to transfer ownership. It should be understood that ownership transfers may be temporary (e.g., in the case of emergency ownership data transfers) or permanent.

As indicated at Block 408, upon receipt of a request to transfer ownership, the data management computing entity 65 is configured to determine whether explicit authorization is required to complete the transfer of ownership. In certain embodiments, one or more user profiles may store data ownership transfer rules that may indicate whether and when explicit authorization is required for transferring ownership. Such data ownership transfer rules may be stored within user profiles associated with ownership of a record data object or an individual data element.

In certain embodiments, the data ownership transfer rules may indicate a default requirement of authorization for data ownership transfers, but may include one or more exceptions, which may be based at least in part on data generated by one or more devices associated with the user. As just one example, upon determining that a wearable device is located within a hospital (e.g., by cross-referencing locations of the wearable device with known hospital locations), and determining that the wearable device indicates that the user is not moving under his/her own power, indicating that the user may be unconscious, the data ownership transfer rules may indicate that data ownership transfers are available to one or more physician users determined to be within a defined radius of the location of the user's wearable device (e.g., determined based at least in part on location data associated with one or more devices associated with various physician user profiles). It should be understood that any of a variety of data ownership transfer rules may be specified for indicating when explicit authorization is required or is not required.

Upon determining that explicit authorization is required, the data management computing entity 65 is configured to generate and provide a notification to a data owner (e.g., a data owner associated with the record data object and/or a data owner associated with the specific data element for which ownership transfer is requested) requesting authorization to transfer ownership of the data element to a specified non-owner. As indicated at Block 410-411, upon receipt of authorization data indicating the requested ownership transfer is approved, the data management computing entity 65 is configured to update ownership data associated with the data element within a data storage repository. As indicated in FIG. 4, if no explicit authorization is required, the data management computing entity 65 is configured to update the ownership data within the data storage repository upon receipt of the initial data ownership transfer request.

f. Data Access and User Interface Generation

Access to view data of a particular data element may be determined based at least in part on data element ownership (e.g., an owner of a particular data element may have viewing access to the data) and/or based at least in part on approvals (e.g., permanent viewing approvals or temporary viewing approvals) provided to a non-owner from the data element owner.

Figure 7:
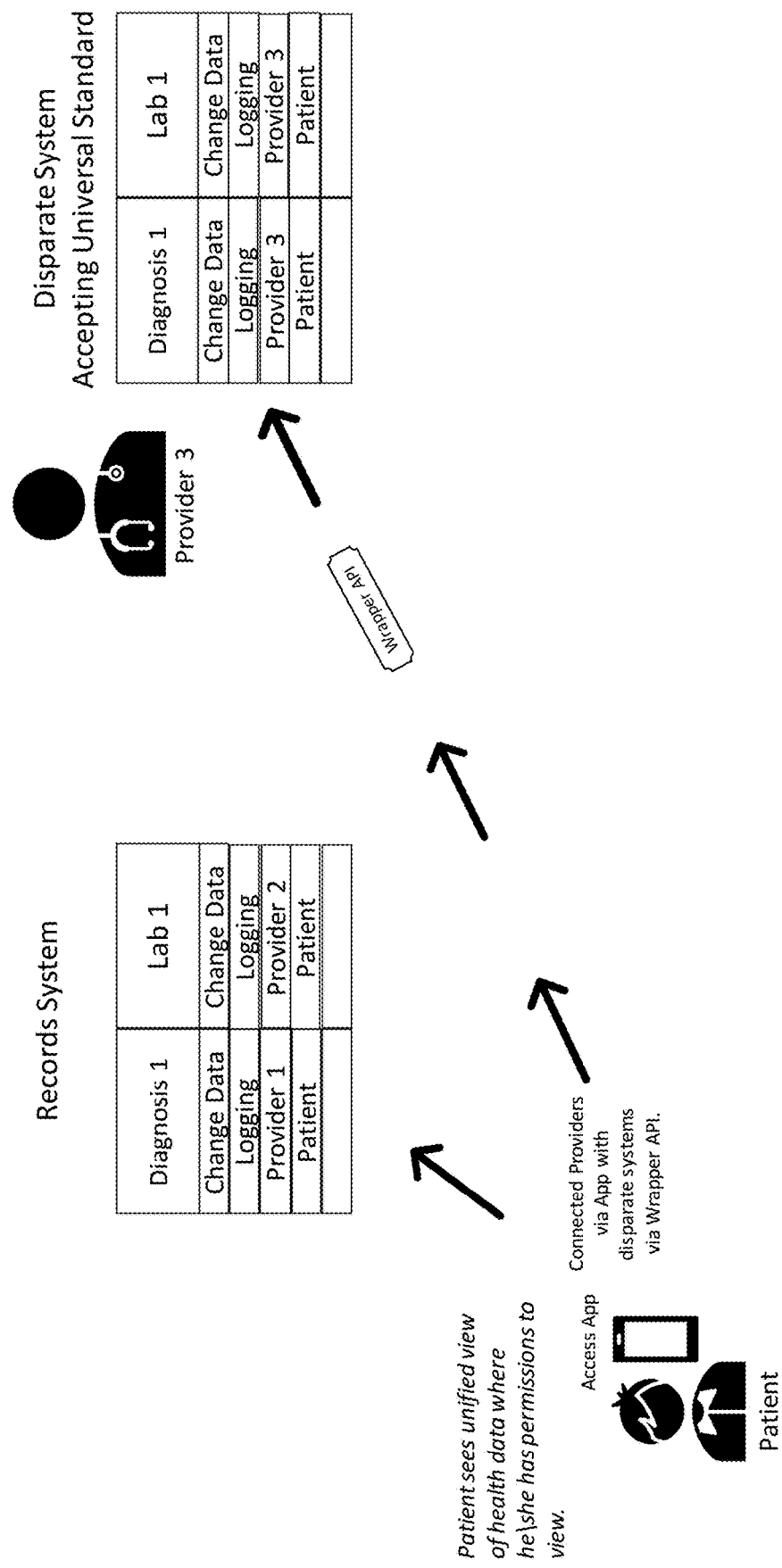
FIG. 7 is a schematic flow diagram illustrating an example process for providing a consolidated user interface based at least in part on data retrieved from disparate storage environments.

Viewing (and, where applicable, editing) of individual data elements may be provided via a corresponding user interface of a record data object. Because such record data objects comprise a plurality of individual data elements, each of which may have corresponding and differing ownership data associated therewith, the generated user interface may be embodied as a composite user interface comprising a plurality of individual data elements (a plurality of those data elements being associated with the record data object) for which the viewer has access. As shown in FIG. 7, the generated composite user interface may comprise data stored in a variety of locations, such as at one or more provider-specific data storage repositories. When a user, such as the patient, requests to view data within a record data object, the data for which the viewing user has access is utilized to generate a composite user interface, which may comprise data retrieved from a plurality of disparate storage areas (e.g., which may be retrieved via appropriate APIs for obtaining data and matching the data with appropriate data tags or other metadata to enable generation of a composite user interface, as shown in FIG. 7).

Generation of the composite user interface may comprise identifying those data elements relating to a record data object for which the requesting user has viewing access (and/or for determining which data elements the requesting viewer has viewing access and which data elements the requesting viewer has read/write access so as to distinguish therebetween), and for constructing a composite user interface (e.g., based at least in part on a template, based at least in part on metadata indicative of relative sizes of graphical representations of each of the data elements to be displayed, and/or the like) for display. Certain embodiments may additionally be configured for receiving a request for access to additional data elements within a record data object, and for generating a request notification to be provided to the data element owner. In such embodiments, if the data element owner provides a responsive approval, the generated user interface may additionally comprise the additional data elements for which the viewer requested access.

Figure 8:
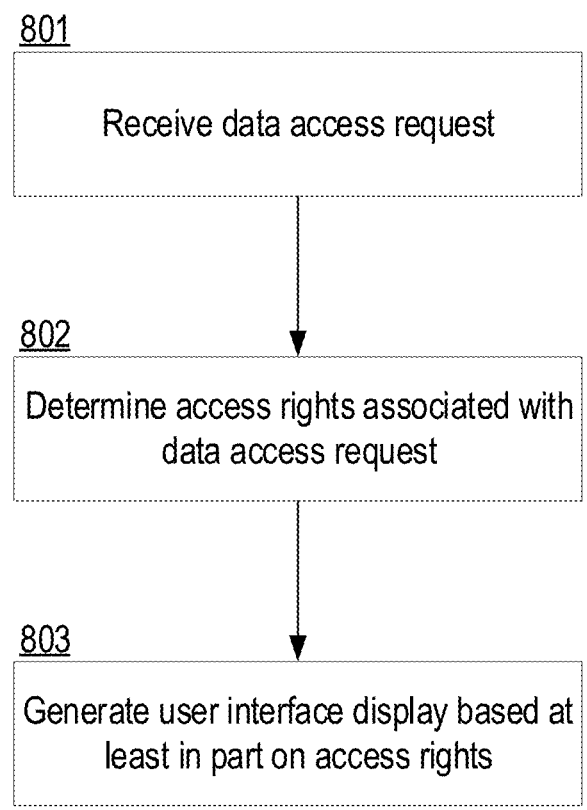
FIG. 8 is a flowchart illustrating an example process for generating a user interface based at least in part on user access rights associated with data.

With reference to FIG. 8, which illustrates an example flowchart associated with generating a user interface associated with a record data object, the process for generating a user interface may begin upon receipt of a data access request, as indicated at Block 801. The data access request may comprise data indicative of a user identifier associated with the requesting user, a record data object for which a user interface is requested, a time stamp associated with the generation of the request, and/or other metadata that may be utilized for determining whether the request is authentic and for determining whether the requesting user has appropriate data access to enable generation of the user interface. In various embodiments, the data access request may be received from a user computing entity 30 associated with the requesting user at the data management computing entity 65.

As indicated at Block 802, the data management computing entity 65 determines data access privileges associated with the requesting user interface and the requested record data object. As discussed herein, such determinations of data access privileges are performed for individual data elements stored in association with the record data object, to determine individual data elements for which the requesting user has access to view (and/or edit). To determine data access privileges, the data management computing entity 65 may be configured to query one or more data access databases comprising data indicative of data access for individual users based at least in part on the requesting user identifier and the requested record data object. The data management computing entity 65 may retrieve a data table (or a portion of a data table) corresponding to the requested record data object and may identify those data elements for which the requesting user has access. It should be understood that other database configurations may be applicable (e.g., graphical databases and/or the like), which may not utilize data tables.

In certain embodiments, the data access request may identify specific data elements for which the requesting user is requesting viewing access. Accordingly, the data management computing entity 65 may determine whether the requesting user has data access privileges to the requested data elements. In other embodiments, the requesting user may specifically identify a particular data element for viewing after generation of the user interface as discussed in greater detail herein. In either event (whether the specific data elements are requested prior to or after generation of the user interface), the data management computing entity 65 is configured to determine whether the requesting user has data access privileges associated with the requested data element. In the event that the requesting user has data access privileges, the data is included within the generated user interface. In the event the requesting user does not have user access privileges, the data management computing entity 65 may generate a notification to the requesting user that the user does not have data access privileges. The data management computing entity 65 may additionally or alternatively generate a data access request notification to be provided to the identified owner of the data element. The data access request notification may comprise data identifying the requesting user, identifying the requested data element, and/or the like, so as to enable the data owner to determine whether access should be permitted to the user. The notification may be provided as a graphical user interface provided to a user computing entity 30 associated with the data owner, which may comprise one or more interactive graphical user interface element which may be selected to grant (or deny) access to the data element. In certain embodiments, the data access request notification may enable the data owner to selectively enable temporary access to the data element (e.g., defined by a number of times the user access the data; defined by an elapsed period of time; defined to expire at a defined expiration time; and/or the like), permanent access to the data element (e.g., defining the requesting user as a co-owner of the data), and/or the like. Upon receipt of data indicating that the data owner has approved access to the requested data element, the data management computing entity 65 additionally retrieves the requested data for inclusion in the composite graphical user interface of the record data object to be provided to the requesting user.

Figure 9:
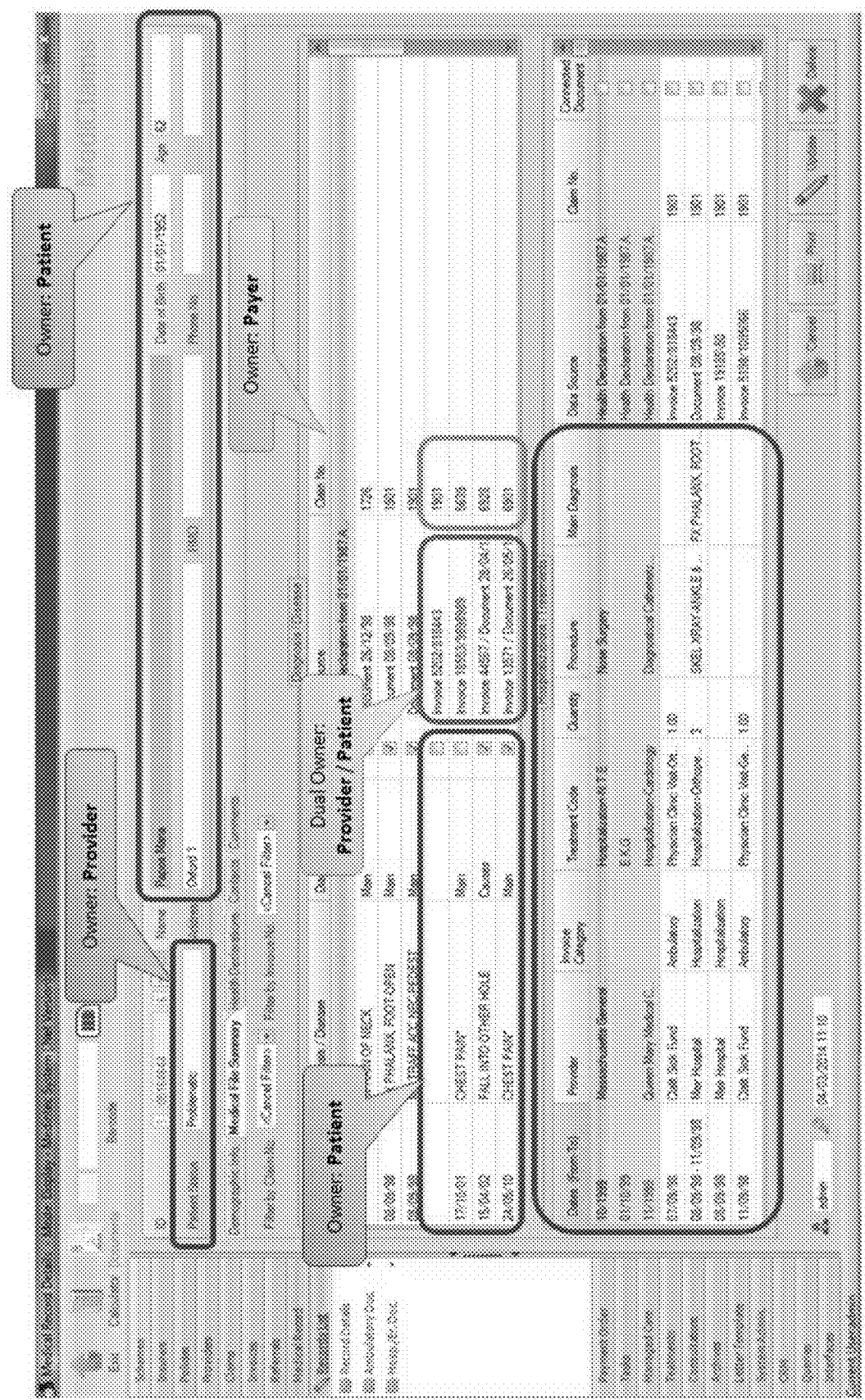
FIG. 9 is an example user interface display according to one embodiment.

As indicated at Block 803 of FIG. 8, the data management computing entity 65 may generate a composite graphical user interface including the data elements for which the requesting user has access relating to the requested record data object. The data management computing entity 65 may generate the composite graphical user interface in real-time, upon receipt of a request. In other embodiments, the data management computing entity 65 may store data indicative of a user-specific template within and/or associated with a record data object. The user-specific template may identify each data element for which the user has access, and the data management computing entity 65 may then populate the template with updated data upon receipt of a viewing request from the user. For example, FIG. 9 is an example of a display containing data elements associated with a plurality of owners. The display of FIG. 9 may be provided to a user having at least temporary access to all of the displayed data elements. Alternatively, FIG. 9 may present an example template identifying locations for display of specific data elements. In embodiments in which FIG. 9 represents a template, one or more of the displayed data elements may be missing (or otherwise hidden) from display if a viewing user does not have access privileges associated with the hidden data elements.

In other embodiments, the data management computing entity 65 may generate a single graphical user interface to be utilized for all viewers of the record data object. The graphical user interface may comprise individual viewing frames, viewing containers, viewing windows, and/or the like corresponding to each data element associated with the record data object. Upon generating a graphical user interface specific to a particular user, those data elements for which the user does not have data access privileges may remain unpopulated, redacted, or otherwise may be missing contents of those graphical user interface elements corresponding to data elements for which the user does not have access. Such a configuration may facilitate users' ability to request access to those otherwise unavailable data elements (e.g., with interactive data elements displayed to the viewing user to request access to those unavailable data elements which are configured to initiate the above-discussed process for generating a data access request notification to the data element owner).

For those embodiments configured for generating the graphical user interface in real-time, the data management computing entity 65 may be configured for reviewing data and/or metadata associated with each data element to be included within the composite graphical user interface so as to determine a most-appropriate ordering for displaying the graphical user interface elements within the generated display. The data management computing entity 65 may apply a graphical user interface generation model, which is configured to satisfy one or more criteria for display of the record data object, such as minimizing the amount of unused space within the display, satisfying one or more user-specific display criteria (e.g., indicating whether specific data windows should be placed), and/or the like.

In certain embodiments, the generated graphical user interface may be interactive, enabling the user to move, resize, or otherwise reconfigure specific user interface elements within the display. Moreover, the data management computing entity 65 may be configured to automatically refresh the generated display upon detecting a change in user access privileges associated with one or more data elements (e.g., to add and/or remove one or more data elements from the generated composite user interface).

Figure 10A:
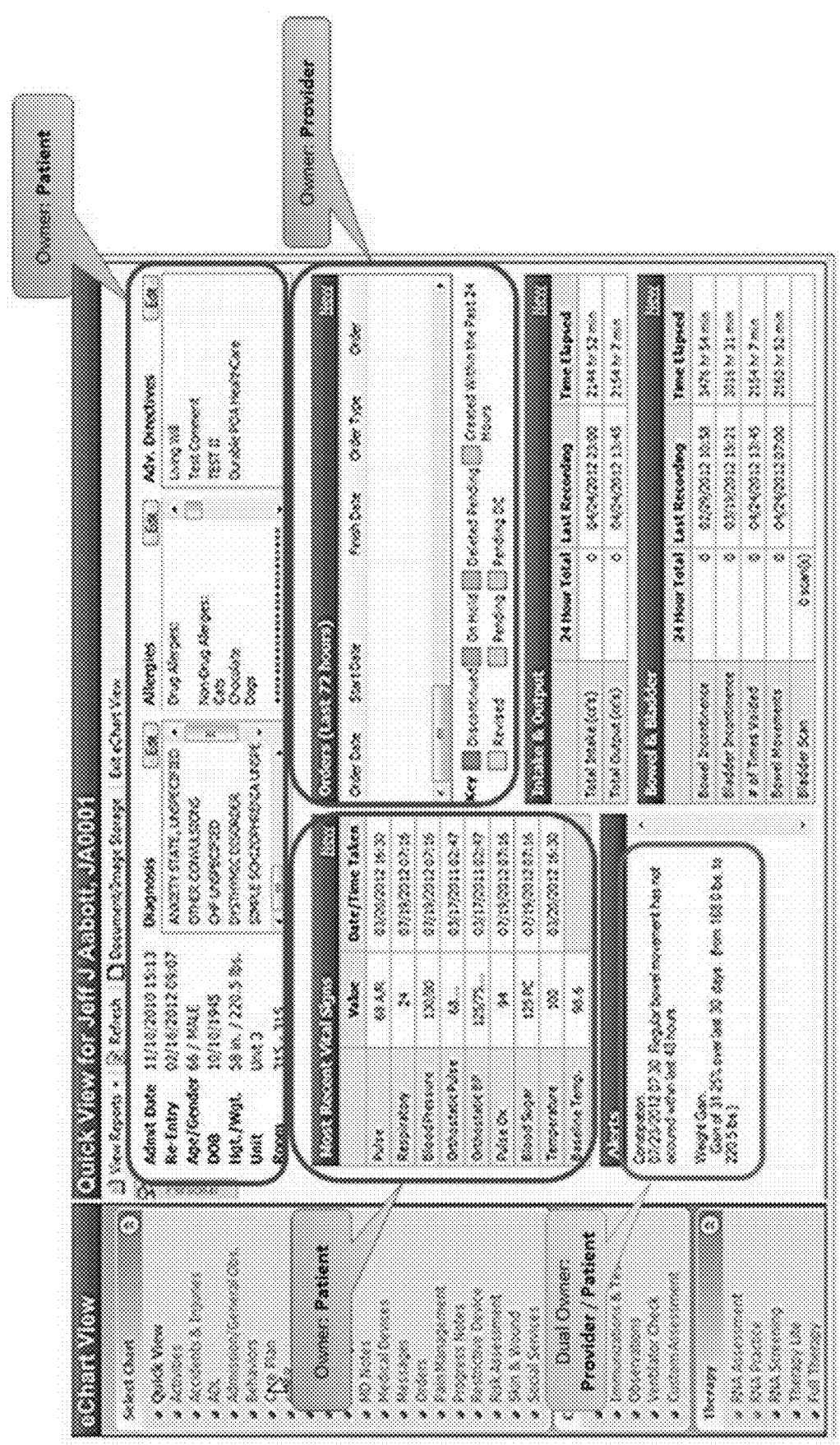
FIGS. 10A-10C are alternative example user interfaces of example data that may be displayed in accordance with certain embodiments.
Figure 10B:
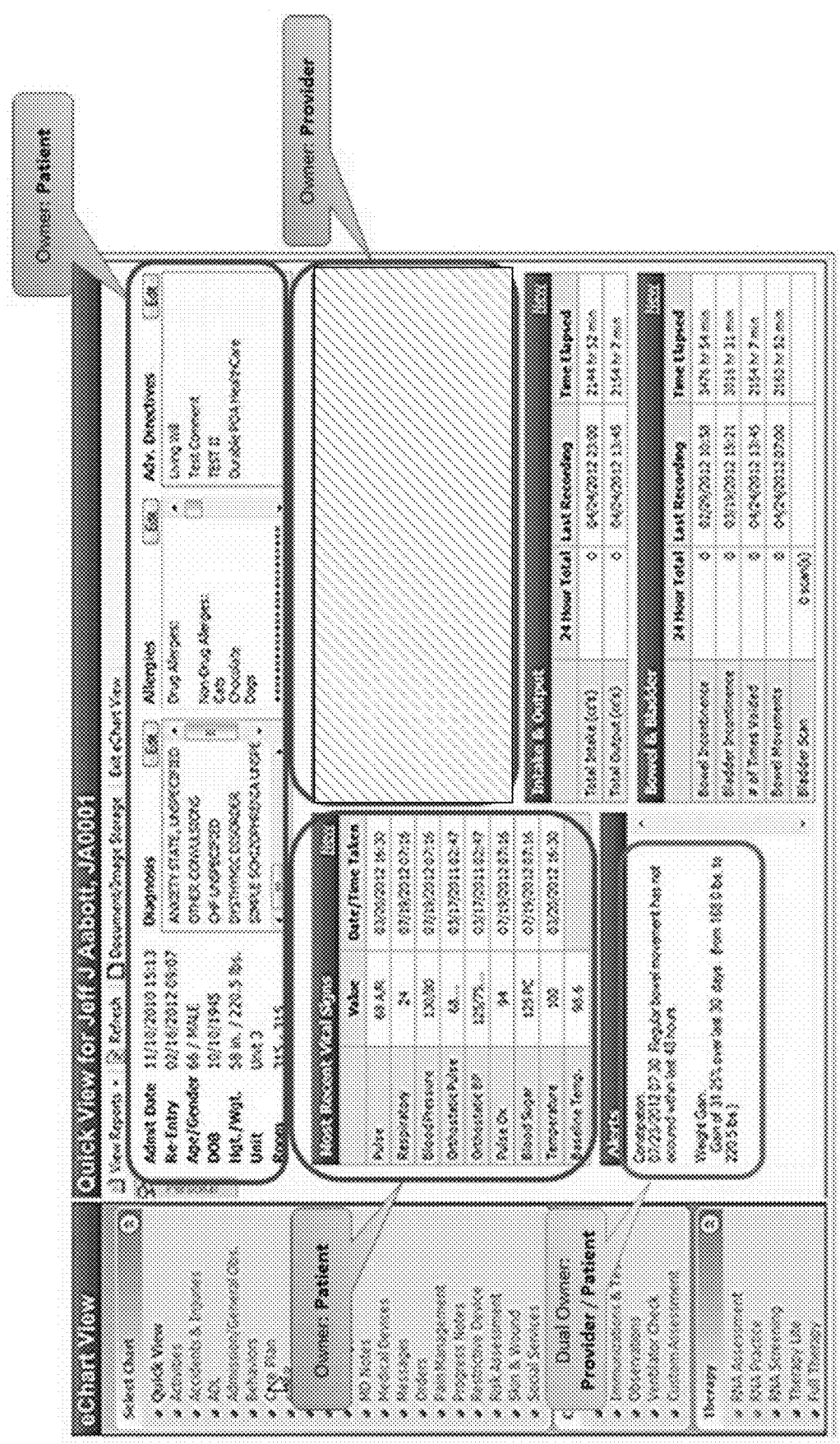
Figure 10C:
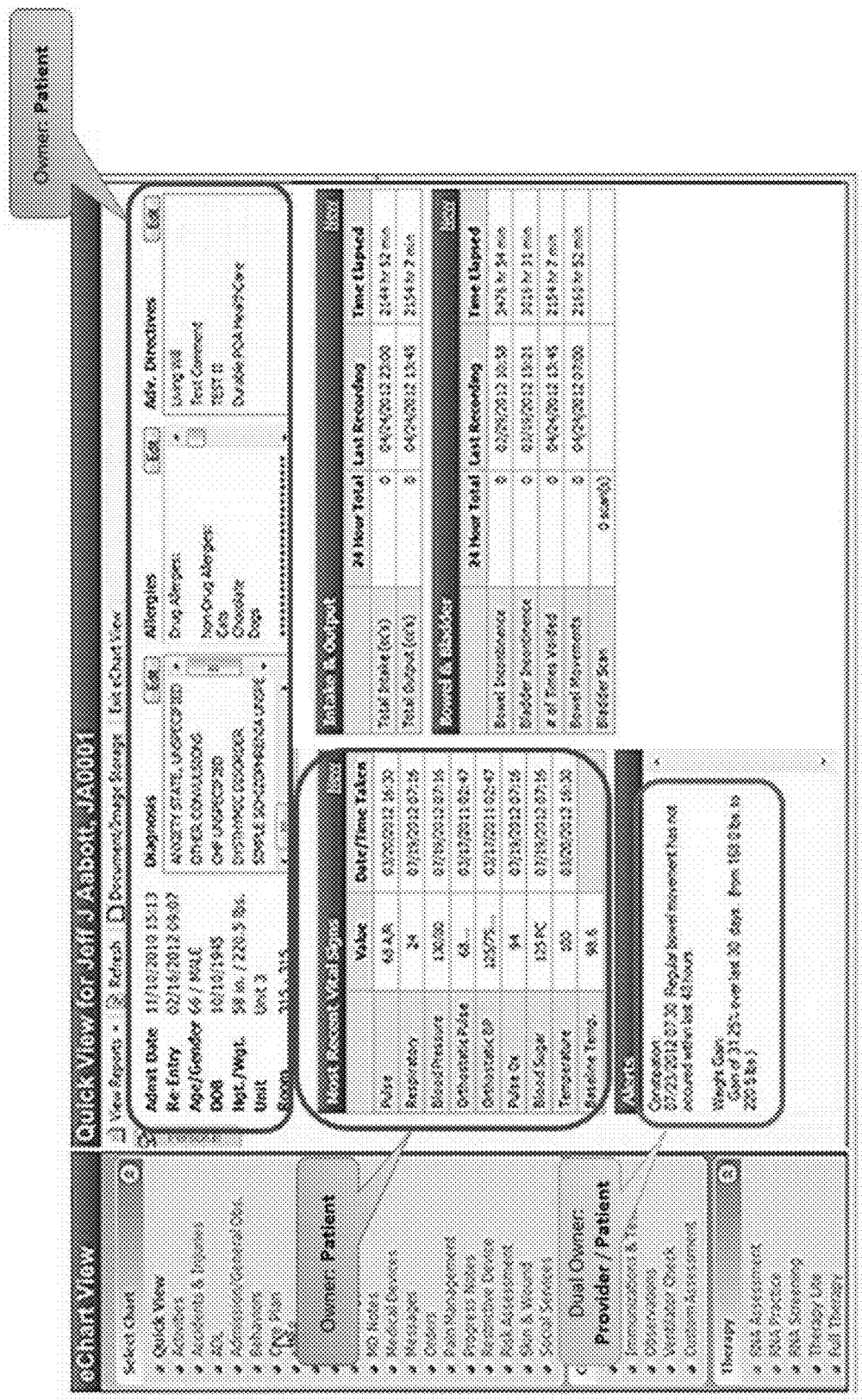

FIGS. 10A-10C illustrate alternative example displays providing a plurality of data elements that may be displayed to a particular user. Specifically, FIG. 10A illustrates all of the data elements relevant to the example record data object, including data owned by the "Patient," data owned by the "Provider," and data owned by both the "Patient" and the "Provider." It should be understood that such a display may be made available to a user having access to both patient-owned and provider-owned data. Alternatively, such a display may be unavailable to any user (accordingly the display of FIG. 10A merely illustrates all of the data elements provided in association with a particular record data object). FIGS. 10B-10C illustrate example displays that may be provided to a patient, illustrating only the data elements for which the patient has access. As shown in FIG. 10B, the provider-owned data may be redacted or otherwise removed from the display, while the existence of such data remains accessible (such that the patient user may see that provider-owned data exists, without seeing the underlying content of the data). Alternatively, as shown in FIG. 10C, the data management computing entity 65 may be configured to rearrange display elements corresponding to the data elements such that only display elements corresponding to data elements for which the patient has access may be displayed. In such embodiments, data elements for which the user does not have access are not displayed, nor are display elements (e.g., display windows) corresponding to the data elements for which the user does not have access.

IV. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An electronic record data object storage system configured for maintaining a plurality of record data objects each comprising a plurality of data elements, the system comprising:
   one or more memory storage repositories storing one or more record data objects each comprising a plurality of data elements, wherein each of the one or more record data objects is associated with a user profile, wherein each of the one or more record data objects comprises ownership data associated with the record data object and access data for each data element stored therein, wherein the access data for each data element has associated ownership data identifying access credentials of the data element, wherein the record data object comprises a first data element identifying first access credentials associated with a first user identifier and a second data element identifying second access credentials associated with a second user identifier, wherein ownership data associated with the each data element can be different from each other and can be different from ownership data associated with the record data object, and wherein the ownership data associated with the each data element is associated with a confidence rating derived from a query directed to the user profile; and
   one or more processors configured to:
      receive a record data object access request for a particular record data object, wherein the record data object access request is associated with a requesting user identifier;
      retrieve access data associated with the particular record data object; and
      generate a user interface for the record data object by:
         identifying one or more authorized data elements from the one or more data elements stored within the particular record data object, wherein the one or more authorized data elements have associated ownership data identifying the requesting user identifier; and
         populating one or more user interface data elements of the user interface with the one or more authorized data elements.

2. The electronic record data object storage system of claim 1, wherein the record data object access request identifies a requested data element of the particular record data object, and wherein the one or more processors are further configured to:
   determine whether the requesting user identifier is identified within the ownership data associated with the requested data element;
   upon determining that the requesting user identifier is identified within the ownership data associated with the requested data element, populate one or more user interface data elements of the user interface with the requested data element;
   upon determining that the requesting user identifier is not identified within the ownership data associated with the requested data element, transmit an access request notification to a user computing entity associated with a user identifier included within the ownership data of the requested data element; and
   upon receipt of an approval response from the user computing entity associated with the user identifier included within the ownership data of the requested data element, populate one or more user interface data elements of the user interface with the requested data element.

3. The electronic record data object storage system of claim 1, wherein the one or more memory storage repositories store the one or more record data objects in one or more relational database tables, wherein each of the one or more data elements are reflected within corresponding entries of the database tables, and wherein the ownership data is reflected within entries associated with the one or more data elements.

4. The electronic record data object storage system of claim 1, where in the one or more memory storage repositories are embodied as distributed memory storage areas, and wherein the one or more processors are associated with a central data management computing entity.

5. The electronic record data object storage system of claim 4, wherein the central data management computing entity additionally comprises data management storage areas storing ownership data corresponding to data elements stored within a plurality of distributed memory storage areas.

6. The electronic record data object storage system of claim 1, wherein the one or more processors are further configured:

receive an ownership transfer request from a user computing entity for a specific data element of a record data object;

determine a current owner of the specific data element;

transmit an ownership transfer request notification to a user computing entity associated with the current owner of the specific data element; and upon receipt of a transfer approval from the user computing entity associated with the current owner of the specific data element, update ownership data associated with the specific data element.

7. The electronic record data object storage system of claim 6, wherein the one or more processors are further configured to, upon receipt of the ownership transfer request for the specific data element of the record data object:

determine a current owner of the record data object;

transmit an ownership transfer request notification to a user computing entity associated with the current owner of the record data object associated with the specific data element; and upon receipt of the transfer approval from the user computing entity associated with the current owner of the specific data element and a second transfer approval from the user computing entity associated with the current owner of the record data object, update ownership data associated with the specific data element.

8. The electronic record data object storage system of claim 1, wherein the one or more processors are further configured to:

receive a new data element from a user computing entity, wherein the new data element has corresponding metadata identifying the user computing entity;

based at least in part on the metadata, identify a record data object corresponding to the data element; and based at least in part on the identified record data object corresponding to the data element and the metadata, identify ownership data corresponding with the new data element.

9. A computer-implemented method for maintaining a plurality of record data objects each comprising a plurality of data elements, the method comprising:

storing, within one or more memory storage repositories, one or more record data objects each comprising a plurality of data elements, wherein each of the one or more record data objects is associated with a user profile, wherein each of the one or more record data objects comprises ownership data associated with the record data object and access data for each data element stored therein, wherein the access data for each data element has associated ownership data identifying access credentials of the data element, wherein the record data object comprises a first data element identifying first access credentials associated with a first user identifier and a second data element identifying second access credentials associated with a second user identifier, and wherein ownership data associated with the each data element can be different from each other and can be different from ownership data associated with the record data object, and wherein the ownership data associated with the each data element is associated with a confidence rating derived from a query directed to the user profile;

receiving, via one or more processors, a record data object access request for a particular record data object, wherein the record data object access request is associated with a requesting user identifier;

retrieving, via the one or more processors, access data associated with the particular record data object; and generating a user interface for the record data object, via the one or more processors, by:

identifying one or more authorized data elements from the one or more data elements stored within the particular record data object, wherein the one or more authorized data elements have associated ownership data identifying the requesting user identifier; and populating one or more user interface data elements of the user interface with the one or more authorized data elements.

10. The computer-implemented method of claim 9, wherein the record data object access request identifies a requested data element of the particular record data object, and wherein the method further comprises:

determining whether the requesting user identifier is identified within the ownership data associated with the requested data element;

upon determining that the requesting user identifier is identified within the ownership data associated with the requested data element, populating one or more user interface data elements of the user interface with the requested data element;

upon determining that the requesting user identifier is not identified within the ownership data associated with the requested data element, transmitting an access request notification to a user computing entity associated with a user identifier included within the ownership data of the requested data element; and upon receipt of an approval response from the user computing entity associated with the user identifier included within the ownership data of the requested data element, populating one or more user interface data elements of the user interface with the requested data element.

11. The computer-implemented method of claim 9, wherein the one or more memory storage repositories store the one or more record data objects in one or more relational database tables, wherein each of the one or more data elements are reflected within corresponding entries of the database tables, and wherein the ownership data is reflected within entries associated with the one or more data elements.

12. The computer-implemented method of claim 9, further comprising:

receiving an ownership transfer request from a user computing entity for a specific data element of a record data object;

determining a current owner of the specific data element;

transmitting an ownership transfer request notification to a user computing entity associated with the current owner of the specific data element; and upon receipt of a transfer approval from the user computing entity associated with the current owner of the specific data element, updating ownership data associated with the specific data element.

13. The computer-implemented method of claim 12, further comprising, upon receipt of the ownership transfer request for the specific data element of the record data object:

determining a current owner of the record data object;

transmitting an ownership transfer request notification to a user computing entity associated with the current owner of the record data object associated with the specific data element; and upon receipt of the transfer approval from the user computing entity associated with the current owner of the specific data element and a second transfer approval from the user computing entity associated with the current owner of the record data object, updating ownership data associated with the specific data element.

14. The computer implemented method of claim 9, further comprising:
receiving a new data element from a user computing entity, wherein the new data element has corresponding metadata identifying the user computing entity;
based at least in part on the metadata, identifying a record data object corresponding to the data element; and
based at least in part on the identified record data object corresponding to the data element and the metadata, identifying ownership data corresponding with the new data element.

15. A computer program product comprising a non-transitory computer readable medium having computer program instructions stored therein, the computer program instructions when executed by a processor, cause the processor to:
store, within one or more memory storage repositories, one or more record data objects each comprising a plurality of data elements, wherein each of the one or more record data objects is associated with a user profile, wherein each of the one or more record data objects comprises ownership data associated with the record data object and access data for each data element stored therein, wherein the access data for each data element has associated ownership data identifying access credentials of the data element, wherein the record data object comprises a first data element identifying first access credentials associated with a first user identifier and a second data element identifying second access credentials associated with a second user identifier, wherein ownership data associated with the each data element can be different from each other and can be different from ownership data associated with the record data object, and wherein the ownership data associated with the each data element is associated with a confidence rating derived from a query directed to the user profile;
receive a record data object access request for a particular record data object, wherein the record data object access request is associated with a requesting user identifier;
retrieve access data associated with the particular record data object; and
generate a user interface for the record data object by:
identifying one or more authorized data elements from the one or more data elements stored within the particular record data object, wherein the one or more authorized data elements have associated ownership data identifying the requesting user identifier; and
populating one or more user interface data elements of the user interface with the one or more authorized data elements.

16. The computer program product of claim 15, wherein the record data object access request identifies a requested data element of the particular record data object, and wherein the computer program instructions when executed by a processor, cause the processor to further:
determine whether the requesting user identifier is identified within the ownership data associated with the requested data element;
upon determining that the requesting user identifier is identified within the ownership data associated with the requested data element, populate one or more user interface data elements of the user interface with the requested data element;
upon determining that the requesting user identifier is not identified within the ownership data associated with the requested data element, transmit an access request notification to a user computing entity associated with a user identifier included within the ownership data of the requested data element; and
upon receipt of an approval response from the user computing entity associated with the user identifier included within the ownership data of the requested data element, populate one or more user interface data elements of the user interface with the requested data element.

17. The computer program product of claim 15, wherein the one or more memory storage repositories store the one or more record data objects in one or more relational database tables, wherein each of the one or more data elements are reflected within corresponding entries of the database tables, and wherein the ownership data is reflected within entries associated with the one or more data elements.

18. The computer program product of claim 15, wherein the computer program instructions when executed by a processor, cause the processor to further:
receive an ownership transfer request from a user computing entity for a specific data element of a record data object;
determine a current owner of the specific data element;
transmit an ownership transfer request notification to a user computing entity associated with the current owner of the specific data element; and
upon receipt of a transfer approval from the user computing entity associated with the current owner of the specific data element, update ownership data associated with the specific data element.

19. The computer program product of claim 17, wherein the computer program instructions when executed by a processor, cause the processor to further, upon receipt of the ownership transfer request for the specific data element of the record data object:
determine a current owner of the record data object;
transmit an ownership transfer request notification to a user computing entity associated with the current owner of the record data object associated with the specific data element; and
upon receipt of the transfer approval from the user computing entity associated with the current owner of the specific data element and a second transfer approval from the user computing entity associated with the current owner of the record data object, update ownership data associated with the specific data element.

20. The computer program product of claim 15, wherein the computer program instructions when executed by a processor, cause the processor to further:
receive a new data element from a user computing entity, wherein the new data element has corresponding metadata identifying the user computing entity;
based at least in part on the metadata, identify a record data object corresponding to the data element; and
based at least in part on the identified record data object corresponding to the data element and the metadata, identify ownership data corresponding with the new data element.

* * * * *

UNITED STATES PATENT AND TRADEMARK OFFICE
CERTIFICATE OF CORRECTION

PATENT NO. : 11,593,348 B2
APPLICATION NO. : 16/803776
DATED : February 28, 2023
INVENTOR(S) : Jon Kevin Muse et al.

It is certified that error appears in the above-identified patent and that said Letters Patent is hereby corrected as shown below:

On the Title Page

Item (72), Inventors, Line 1, delete "Thompson Station," and insert -- Thompson's Station, --, therefor.

In the Claims

In Column 34, Line 55, Claim 4, delete "where in" and insert -- wherein --, therefor.

In Column 35, Line 57, Claim 9, delete "identifier, and wherein" and insert -- identifier, wherein --, therefor.

In Column 37, Line 7, Claim 14, delete "computer implemented" and insert -- computer-implemented --, therefor.

Signed and Sealed this
Fifth Day of September, 2023

Katherine Kelly Vidal
*Director of the United States Patent and Trademark Office*